US008685441B2

(12) United States Patent
Hui et al.

(10) Patent No.: US 8,685,441 B2
(45) Date of Patent: *Apr. 1, 2014

(54) PREPARATION OF A LIPID BLEND AND A PHOSPHOLIPID SUSPENSION CONTAINING THE LIPID BLEND

(71) Applicant: Lantheus Medical Imaging, Inc., North Billerica, MA (US)

(72) Inventors: Poh K. Hui, Wellesley Hills, MA (US); John E. Bishop, Groton, MA (US); Eleodoro S. Madrigal, Jr., Westford, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,105

(22) Filed: Jul. 23, 2013

(65) Prior Publication Data
US 2013/0309174 A1 Nov. 21, 2013

Related U.S. Application Data

(60) Continuation of application No. 13/195,734, filed on Aug. 1, 2011, which is a division of application No. 10/667,931, filed on Sep. 22, 2003, now Pat. No. 8,084,056, which is a continuation of application No. 09/229,258, filed on Jan. 13, 1999, now abandoned.

(60) Provisional application No. 60/071,332, filed on Jan. 14, 1998.

(51) Int. Cl.
*A61K 9/127* (2006.01)
(52) U.S. Cl.
USPC .......... 424/450; 424/9.51; 424/9.52; 264/4.1; 264/4.3
(58) Field of Classification Search
USPC ....................................................... 424/450
See application file for complete search history.

(56) References Cited

U.S. PATENT DOCUMENTS

| | | |
|---|---|---|
| 3,015,128 A | 1/1962 | Sommerville et al. |
| 3,291,843 A | 12/1966 | Fritz et al. |
| 3,293,114 A | 12/1966 | Kenaga et al. |
| 3,479,811 A | 11/1969 | Walters |
| 3,488,714 A | 1/1970 | Walters et al. |
| 3,532,500 A | 10/1970 | Priest et al. |
| 3,557,294 A | 1/1971 | Dear et al. |
| 3,594,326 A | 7/1971 | Himmel et al. |
| 3,615,972 A | 10/1971 | Morehouse, Jr. et al. |
| 3,650,831 A | 3/1972 | Jungermann et al. |
| 3,732,172 A | 5/1973 | Herbig et al. |
| 3,873,564 A | 3/1975 | Schneider et al. |
| 3,945,956 A | 3/1976 | Garner |
| 3,960,583 A | 6/1976 | Netting et al. |
| 3,968,203 A | 7/1976 | Spitzer et al. |
| 4,004,384 A | 1/1977 | Hood |
| 4,027,007 A | 5/1977 | Messina |
| 4,089,801 A | 5/1978 | Schneider |
| 4,108,806 A | 8/1978 | Cohrs et al. |
| 4,138,383 A | 2/1979 | Rembaum et al. |
| 4,162,282 A | 7/1979 | Fulwyler et al. |
| 4,179,546 A | 12/1979 | Garner et al. |
| 4,192,859 A | 3/1980 | Mackaness et al. |
| 4,224,179 A | 9/1980 | Schneider |
| 4,229,360 A | 10/1980 | Schneider et al. |
| 4,235,871 A | 11/1980 | Papahadjopoulos et al. |
| 4,265,251 A | 5/1981 | Tickner |
| 4,276,885 A | 7/1981 | Tickner et al. |
| 4,303,736 A | 12/1981 | Torobin |
| 4,310,505 A | 1/1982 | Baldeschwieler et al. |
| 4,310,506 A | 1/1982 | Baldeschwieler et al. |
| 4,315,514 A | 2/1982 | Drewes et al. |
| 4,331,654 A | 5/1982 | Morris |
| 4,342,826 A | 8/1982 | Cole |
| 4,344,929 A | 8/1982 | Bonsen et al. |
| 4,420,442 A | 12/1983 | Sands |
| 4,421,562 A | 12/1983 | Sands |
| 4,426,330 A | 1/1984 | Sears |
| 4,427,649 A | 1/1984 | Dingle et al. |
| 4,428,924 A | 1/1984 | Millington |
| 4,442,843 A | 4/1984 | Rasor et al. |
| 4,466,442 A | 8/1984 | Hilmann et al. |
| 4,474,773 A | 10/1984 | Shinitzky et al. |
| 4,485,193 A | 11/1984 | Rubens et al. |
| 4,515,736 A | 5/1985 | Deamer |
| 4,522,803 A | 6/1985 | Lenk et al. |

(Continued)

FOREIGN PATENT DOCUMENTS

| | | |
|---|---|---|
| AU | B-30351/89 | 3/1993 |
| AU | 641363 B2 | 9/1993 |

(Continued)

OTHER PUBLICATIONS

"'Freon' Fluorocarbons: Properties and Applications" in DuPont Technical Bulletin G-1 (E.I. DuPont de Nemours and Company, Wilmington, DE), pp. 1-10 (1987).
"Concise Encylcopedia of Polymer Science and Engineering," J. Kroschwitz, ed., John Wiley & Sons, New York, pp. 12-13 (1990).
"Encyclopedia of Polymer Sciences and Engineering," John Wiley & Sons, New York, 1:164-169 (1985).
"Properties and Applications of the 'Freon' Fluorocarbons" in DuPont Freon Technical Bulletin B-2 (E.I. DuPont de Nemours and Company, Wilmington, DE), pp. 1-11 (1964).
[No Author Listed] Division of new drug chemistry document relating to Definity. Review date, Feb. 15, 2001.

(Continued)

*Primary Examiner* — Gollamudi Kishore
(74) *Attorney, Agent, or Firm* — Wolf, Greenfield & Sacks, P.C.

(57) ABSTRACT

The present invention describes processes for the preparation of a lipid blend and a uniform filterable phospholipid suspension containing the lipid blend, such suspension being useful as an ultrasound contrast agent.

28 Claims, No Drawings

(56) References Cited

U.S. PATENT DOCUMENTS

| | | |
|---|---|---|
| 4,530,360 A | 7/1985 | Duarte |
| 4,533,254 A | 8/1985 | Cook et al. |
| 4,534,899 A | 8/1985 | Sears |
| 4,540,629 A | 9/1985 | Sands et al. |
| 4,544,545 A | 10/1985 | Ryan et al. |
| 4,549,892 A | 10/1985 | Baker et al. |
| 4,569,836 A | 2/1986 | Gordon |
| 4,572,203 A | 2/1986 | Feinstein |
| 4,582,756 A | 4/1986 | Niinuma et al. |
| 4,586,512 A | 5/1986 | Do-huu et al. |
| 4,603,044 A | 7/1986 | Geho et al. |
| 4,615,879 A | 10/1986 | Runge et al. |
| 4,620,546 A | 11/1986 | Aida et al. |
| 4,621,023 A | 11/1986 | Redziniak et al. |
| 4,636,381 A | 1/1987 | Takada et al. |
| 4,646,756 A | 3/1987 | Watmough et al. |
| 4,657,756 A | 4/1987 | Rasor et al. |
| 4,658,828 A | 4/1987 | Dory |
| 4,663,161 A | 5/1987 | Mannino et al. |
| 4,675,310 A | 6/1987 | Chapman et al. |
| 4,680,171 A | 7/1987 | Shell |
| 4,681,119 A | 7/1987 | Rasor et al. |
| 4,683,092 A | 7/1987 | Tsang |
| 4,684,479 A | 8/1987 | D'Arrigo |
| 4,687,661 A | 8/1987 | Kikuchi et al. |
| 4,689,986 A | 9/1987 | Carson et al. |
| 4,693,999 A | 9/1987 | Axelsson et al. |
| 4,718,433 A | 1/1988 | Feinstein |
| 4,722,943 A | 2/1988 | Melber et al. |
| 4,728,575 A | 3/1988 | Gamble et al. |
| 4,728,578 A | 3/1988 | Higgins et al. |
| 4,731,239 A | 3/1988 | Gordon |
| 4,737,323 A | 4/1988 | Martin et al. |
| 4,748,216 A | 5/1988 | Tom |
| 4,753,788 A | 6/1988 | Gamble |
| 4,761,288 A | 8/1988 | Mezei |
| 4,767,610 A | 8/1988 | Long |
| 4,774,958 A | 10/1988 | Feinstein |
| 4,775,522 A | 10/1988 | Clark, Jr. |
| 4,776,991 A | 10/1988 | Farmer et al. |
| 4,781,871 A | 11/1988 | West, III et al. |
| 4,789,501 A | 12/1988 | Day et al. |
| 4,790,891 A | 12/1988 | Halliday et al. |
| 4,822,534 A | 4/1989 | Lencki et al. |
| 4,830,858 A | 5/1989 | Payne et al. |
| 4,832,941 A | 5/1989 | Berwing et al. |
| 4,834,964 A | 5/1989 | Rosen |
| 4,844,882 A | 7/1989 | Widder et al. |
| 4,863,717 A | 9/1989 | Keana |
| 4,863,740 A | 9/1989 | Kissel et al. |
| 4,865,836 A | 9/1989 | Long, Jr. |
| 4,866,096 A | 9/1989 | Schweighardt |
| 4,873,035 A | 10/1989 | Wong |
| 4,877,561 A | 10/1989 | Iga et al. |
| 4,880,635 A | 11/1989 | Janoff et al. |
| 4,893,624 A | 1/1990 | Lele |
| 4,895,719 A | 1/1990 | Radhakrishnan et al. |
| 4,895,876 A | 1/1990 | Schweighardt et al. |
| 4,898,734 A | 2/1990 | Mathiowitz et al. |
| 4,900,540 A | 2/1990 | Ryan et al. |
| 4,918,065 A | 4/1990 | Stindl et al. |
| 4,919,895 A | 4/1990 | Heldebrant et al. |
| 4,921,706 A | 5/1990 | Roberts et al. |
| 4,927,623 A | 5/1990 | Long, Jr. |
| 4,933,121 A | 6/1990 | Law et al. |
| 4,938,947 A | 7/1990 | Nicolau et al. |
| 4,946,787 A | 8/1990 | Eppstein et al. |
| 4,957,656 A | 9/1990 | Cerny et al. |
| 4,972,002 A | 11/1990 | Volkert |
| 4,978,483 A | 12/1990 | Redding, Jr. |
| 4,981,692 A | 1/1991 | Popescu et al. |
| 4,984,573 A | 1/1991 | Leunbach |
| 4,985,550 A | 1/1991 | Charpiot et al. |
| 4,987,154 A | 1/1991 | Long, Jr. |
| 4,993,415 A | 2/1991 | Long |
| 4,996,041 A | 2/1991 | Arai et al. |
| 5,000,960 A | 3/1991 | Wallach |
| 5,004,611 A | 4/1991 | Leigh |
| 5,006,343 A | 4/1991 | Benson et al. |
| 5,008,050 A | 4/1991 | Cullis et al. |
| 5,008,109 A | 4/1991 | Tin |
| 5,013,556 A | 5/1991 | Woodle et al. |
| 5,019,370 A | 5/1991 | Jay et al. |
| 5,045,304 A | 9/1991 | Schneider et al. |
| 5,049,322 A | 9/1991 | Devissaguet et al. |
| 5,049,388 A | 9/1991 | Knight et al. |
| 5,053,214 A | 10/1991 | Jada |
| 5,053,217 A | 10/1991 | Lehigh |
| 5,077,036 A | 12/1991 | Long, Jr. |
| 5,078,994 A | 1/1992 | Nair et al. |
| 5,080,885 A | 1/1992 | Long, Jr. |
| 5,088,499 A | 2/1992 | Unger |
| 5,089,181 A | 2/1992 | Hauser |
| 5,091,188 A | 2/1992 | Haynes |
| 5,100,662 A | 3/1992 | Bolcsak et al. |
| 5,107,842 A | 4/1992 | Levene et al. |
| 5,114,703 A | 5/1992 | Wolf et al. |
| 5,123,414 A | 6/1992 | Unger |
| 5,135,000 A | 8/1992 | Akselrod et al. |
| 5,137,928 A | 8/1992 | Erbel et al. |
| 5,141,738 A | 8/1992 | Rasor et al. |
| 5,147,631 A | 9/1992 | Glajch et al. |
| 5,149,319 A | 9/1992 | Unger |
| 5,171,577 A | 12/1992 | Griat et al. |
| 5,171,678 A | 12/1992 | Behr et al. |
| 5,171,755 A | 12/1992 | Kaufman et al. |
| 5,174,930 A | 12/1992 | Stainmesse et al. |
| 5,186,922 A | 2/1993 | Shell et al. |
| 5,190,766 A | 3/1993 | Ishihara |
| 5,190,982 A | 3/1993 | Erbel et al. |
| 5,192,549 A | 3/1993 | Barenolz et al. |
| 5,194,188 A | 3/1993 | Guitierrez |
| 5,194,266 A | 3/1993 | Abra et al. |
| 5,195,520 A | 3/1993 | Schlief et al. |
| 5,196,183 A | 3/1993 | Yudelson et al. |
| 5,196,348 A | 3/1993 | Schweighardt et al. |
| 5,198,225 A | 3/1993 | Meybeck et al. |
| 5,205,287 A | 4/1993 | Erbel et al. |
| 5,205,290 A | 4/1993 | Unger |
| 5,209,720 A | 5/1993 | Unger |
| 5,213,804 A | 5/1993 | Martin et al. |
| 5,215,680 A | 6/1993 | D'Arrigo |
| 5,219,538 A | 6/1993 | Henderson et al. |
| 5,228,446 A | 7/1993 | Unger et al. |
| 5,230,882 A | 7/1993 | Unger |
| 5,246,707 A | 9/1993 | Haynes |
| 5,247,935 A | 9/1993 | Cline et al. |
| 5,264,618 A | 11/1993 | Felgner et al. |
| 5,271,928 A | 12/1993 | Schneider et al. |
| 5,279,833 A | 1/1994 | Rose |
| 5,281,408 A | 1/1994 | Unger |
| 5,283,185 A | 2/1994 | Epand et al. |
| 5,283,255 A | 2/1994 | Levy et al. |
| 5,305,757 A | 4/1994 | Unger et al. |
| 5,310,540 A | 5/1994 | Giddey et al. |
| 5,315,997 A | 5/1994 | Widder et al. |
| 5,315,998 A | 5/1994 | Tachibana et al. |
| 5,316,771 A | 5/1994 | Barenholz et al. |
| 5,326,552 A | 7/1994 | Na et al. |
| 5,334,381 A | 8/1994 | Unger |
| 5,334,761 A | 8/1994 | Gebeyehu et al. |
| 5,339,814 A | 8/1994 | Lasker |
| 5,344,930 A | 9/1994 | Riess et al. |
| 5,348,016 A | 9/1994 | Unger et al. |
| 5,350,571 A | 9/1994 | Kaufman et al. |
| 5,352,435 A | 10/1994 | Unger |
| 5,354,549 A | 10/1994 | Klaveness et al. |
| 5,358,702 A | 10/1994 | Unger |
| 5,362,477 A | 11/1994 | Moore et al. |
| 5,362,478 A | 11/1994 | Desai et al. |
| 5,368,840 A | 11/1994 | Unger |
| 5,380,411 A | 1/1995 | Schlief |
| 5,380,519 A | 1/1995 | Schneider et al. |
| 5,393,513 A | 2/1995 | Long, Jr. |

(56) References Cited

U.S. PATENT DOCUMENTS

| | | |
|---|---|---|
| 5,393,524 A | 2/1995 | Quay |
| 5,403,575 A | 4/1995 | Kaufman et al. |
| 5,409,688 A | 4/1995 | Quay |
| 5,410,516 A | 4/1995 | Uhlendorf et al. |
| 5,413,774 A | 5/1995 | Schneider et al. |
| 5,425,366 A | 6/1995 | Reinhardt et al. |
| 5,433,204 A | 7/1995 | Olson |
| 5,445,813 A | 8/1995 | Schneider et al. |
| 5,456,900 A | 10/1995 | Unger |
| 5,456,901 A | 10/1995 | Unger |
| 5,460,800 A | 10/1995 | Walters |
| 5,469,854 A | 11/1995 | Unger et al. |
| 5,470,582 A | 11/1995 | Supersaxo et al. |
| 5,485,839 A | 1/1996 | Aida et al. |
| 5,487,390 A | 1/1996 | Cohen et al. |
| 5,496,535 A | 3/1996 | Kirkland |
| 5,496,536 A | 3/1996 | Wolf |
| 5,498,421 A | 3/1996 | Grinstaff et al. |
| 5,501,863 A | 3/1996 | Rossling et al. |
| 5,502,094 A | 3/1996 | Moore et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,514,720 A | 5/1996 | Clark, Jr. et al. |
| 5,527,521 A | 6/1996 | Unger |
| 5,529,766 A | 6/1996 | Klaveness et al. |
| 5,531,980 A | 7/1996 | Schneider et al. |
| 5,533,217 A | 7/1996 | Holdredge |
| 5,536,489 A | 7/1996 | Lohrmann et al. |
| 5,536,490 A | 7/1996 | Klaveness et al. |
| 5,536,753 A | 7/1996 | Clark, Jr. |
| 5,539,814 A | 7/1996 | Shoji |
| 5,540,909 A | 7/1996 | Schutt |
| 5,542,935 A | 8/1996 | Unger et al. |
| 5,545,396 A | 8/1996 | Albert et al. |
| 5,547,656 A | 8/1996 | Unger |
| 5,552,133 A | 9/1996 | Lambert et al. |
| 5,552,155 A | 9/1996 | Bailey et al. |
| 5,556,372 A | 9/1996 | Talish et al. |
| 5,556,610 A | 9/1996 | Yan et al. |
| 5,558,092 A | 9/1996 | Unger et al. |
| 5,558,094 A | 9/1996 | Quay |
| 5,558,853 A | 9/1996 | Quay |
| 5,558,854 A | 9/1996 | Quay |
| 5,558,855 A | 9/1996 | Quay |
| 5,558,856 A | 9/1996 | Klaveness et al. |
| 5,560,364 A | 10/1996 | Porter |
| 5,562,608 A | 10/1996 | Sekins et al. |
| 5,562,893 A | 10/1996 | Lohrmann |
| 5,565,215 A | 10/1996 | Gref et al. |
| 5,567,412 A | 10/1996 | Klaveness et al. |
| 5,567,413 A | 10/1996 | Klaveness et al. |
| 5,567,414 A | 10/1996 | Schneider et al. |
| 5,567,415 A | 10/1996 | Porter |
| 5,567,765 A | 10/1996 | Moore et al. |
| 5,569,448 A | 10/1996 | Wong et al. |
| 5,569,449 A | 10/1996 | Klaveness et al. |
| 5,571,497 A | 11/1996 | Unger |
| 5,571,498 A | 11/1996 | Cacheris et al. |
| 5,571,797 A | 11/1996 | Ohno et al. |
| 5,573,751 A | 11/1996 | Quay |
| 5,578,292 A | 11/1996 | Schneider et al. |
| 5,580,575 A | 12/1996 | Unger et al. |
| 5,585,112 A * | 12/1996 | Unger et al. ............ 424/450 |
| 5,593,680 A | 1/1997 | Bara et al. |
| 5,595,723 A | 1/1997 | Quay |
| 5,605,673 A | 2/1997 | Schutt et al. |
| 5,606,973 A | 3/1997 | Lambert et al. |
| 5,607,661 A | 3/1997 | Berg et al. |
| 5,612,057 A | 3/1997 | Lanza et al. |
| 5,612,318 A | 3/1997 | Weichselbaum et al. |
| 5,614,169 A | 3/1997 | Klaveness et al. |
| 5,620,689 A | 4/1997 | Allen et al. |
| 5,626,833 A | 5/1997 | Schutt et al. |
| 5,635,539 A | 6/1997 | Clark, Jr. et al. |
| 5,637,289 A | 6/1997 | Klaveness et al. |
| 5,639,443 A | 6/1997 | Schutt et al. |
| 5,639,473 A | 6/1997 | Grinstaff et al. |
| 5,643,553 A | 7/1997 | Schneider et al. |
| 5,648,095 A | 7/1997 | Illum et al. |
| 5,648,098 A | 7/1997 | Porter |
| 5,656,211 A | 8/1997 | Unger et al. |
| 5,662,931 A | 9/1997 | Munechika et al. |
| 5,667,472 A | 9/1997 | Finn et al. |
| 5,672,585 A | 9/1997 | Pierschbacher et al. |
| 5,676,928 A | 10/1997 | Klaveness et al. |
| 5,677,472 A * | 10/1997 | Nyberg et al. ............ 554/20 |
| 5,679,459 A | 10/1997 | Riess et al. |
| 5,686,060 A | 11/1997 | Schneider et al. |
| 5,686,102 A | 11/1997 | Gross et al. |
| 5,695,460 A | 12/1997 | Siegel et al. |
| 5,695,741 A | 12/1997 | Schutt et al. |
| 5,701,899 A | 12/1997 | Porter |
| 5,705,187 A | 1/1998 | Unger |
| 5,707,352 A | 1/1998 | Sekins et al. |
| 5,707,606 A | 1/1998 | Quay |
| 5,707,607 A | 1/1998 | Quay |
| 5,711,933 A | 1/1998 | Bichon et al. |
| 5,715,824 A | 2/1998 | Unger et al. |
| 5,716,597 A | 2/1998 | Lohrmann et al. |
| 5,730,954 A | 3/1998 | Albayrak et al. |
| 5,732,707 A | 3/1998 | Widder et al. |
| 5,733,527 A | 3/1998 | Schutt |
| 5,733,572 A | 3/1998 | Unger et al. |
| 5,736,121 A | 4/1998 | Unger |
| 5,740,807 A | 4/1998 | Porter |
| 5,741,513 A | 4/1998 | Ghyczy et al. |
| 5,769,080 A | 6/1998 | Unger et al. |
| 5,770,222 A | 6/1998 | Unger et al. |
| 5,773,024 A | 6/1998 | Unger et al. |
| 5,776,429 A | 7/1998 | Unger et al. |
| 5,785,950 A | 7/1998 | Kaufman et al. |
| 5,798,091 A | 8/1998 | Trevino et al. |
| 5,804,162 A | 9/1998 | Kabalnov et al. |
| 5,820,873 A * | 10/1998 | Choi et al. ............ 424/283.1 |
| 5,830,430 A | 11/1998 | Unger et al. |
| 5,840,023 A | 11/1998 | Oraevsky et al. |
| 5,840,661 A | 11/1998 | Fischer et al. |
| 5,846,517 A | 12/1998 | Unger |
| 5,849,727 A | 12/1998 | Porter et al. |
| 5,853,752 A | 12/1998 | Unger et al. |
| 5,855,865 A | 1/1999 | Lambert et al. |
| 5,858,399 A | 1/1999 | Lanza et al. |
| 5,874,062 A | 2/1999 | Unger |
| 5,879,659 A | 3/1999 | Edwards et al. |
| 5,897,851 A | 4/1999 | Quay et al. |
| 5,922,304 A | 7/1999 | Unger |
| 5,935,553 A | 8/1999 | Unger et al. |
| 5,958,371 A | 9/1999 | Lanza et al. |
| 5,965,109 A | 10/1999 | Lohrmann |
| 5,965,158 A | 10/1999 | Link et al. |
| 5,976,501 A | 11/1999 | Jablonski |
| 5,980,936 A | 11/1999 | Krafft et al. |
| 5,985,246 A | 11/1999 | Unger |
| 5,989,520 A | 11/1999 | Lanza et al. |
| 5,997,898 A | 12/1999 | Unger |
| 6,001,335 A | 12/1999 | Unger |
| 6,027,726 A * | 2/2000 | Ansell ............ 424/180.1 |
| 6,028,066 A | 2/2000 | Unger |
| 6,033,645 A | 3/2000 | Unger et al. |
| 6,033,646 A | 3/2000 | Unger et al. |
| 6,039,557 A | 3/2000 | Unger et al. |
| 6,056,938 A | 5/2000 | Unger et al. |
| 6,068,857 A | 5/2000 | Weitschies et al. |
| 6,071,494 A | 6/2000 | Unger |
| 6,071,495 A | 6/2000 | Unger et al. |
| 6,086,573 A | 7/2000 | Siegel et al. |
| 6,088,613 A | 7/2000 | Unger |
| 6,090,800 A | 7/2000 | Unger et al. |
| 6,117,414 A | 9/2000 | Unger |
| 6,123,923 A | 9/2000 | Unger et al. |
| 6,139,819 A | 10/2000 | Unger et al. |
| 6,143,276 A | 11/2000 | Unger |
| 6,146,657 A | 11/2000 | Unger et al. |

(56) References Cited

U.S. PATENT DOCUMENTS

| | | |
|---|---|---|
| 6,150,304 A | 11/2000 | Fischer et al. |
| 6,159,445 A | 12/2000 | Klaveness et al. |
| 6,165,442 A | 12/2000 | Swaerd-Nordmo et al. |
| 6,210,707 B1 | 4/2001 | Papahadjopoulos et al. |
| 6,231,834 B1 | 5/2001 | Unger et al. |
| 6,254,852 B1 | 7/2001 | Glajch et al. |
| 6,258,378 B1 | 7/2001 | Schneider et al. |
| 6,261,231 B1 | 7/2001 | Damphousse et al. |
| 6,261,537 B1 | 7/2001 | Klaveness et al. |
| 6,315,981 B1 | 11/2001 | Unger |
| 6,331,289 B1 | 12/2001 | Klaveness et al. |
| 6,414,139 B1 | 7/2002 | Unger et al. |
| 6,416,740 B1 | 7/2002 | Unger |
| 6,443,898 B1 | 9/2002 | Unger et al. |
| 6,444,660 B1 | 9/2002 | Unger et al. |
| 6,455,277 B1 | 9/2002 | Fox et al. |
| 6,461,586 B1 | 10/2002 | Unger |
| 6,479,034 B1 | 11/2002 | Unger et al. |
| 6,521,211 B1 | 2/2003 | Unger et al. |
| 6,528,039 B2 | 3/2003 | Unger |
| 6,537,246 B1 | 3/2003 | Unger et al. |
| 6,548,047 B1 | 4/2003 | Unger |
| 6,551,576 B1 | 4/2003 | Unger et al. |
| 6,572,840 B1 | 6/2003 | Toler |
| 6,576,220 B2 | 6/2003 | Unger |
| 6,635,017 B1 | 10/2003 | Moehring et al. |
| 6,680,047 B2 | 1/2004 | Klaveness et al. |
| 6,682,502 B2 | 1/2004 | Bond et al. |
| 6,716,412 B2 | 4/2004 | Unger |
| 6,773,696 B2 | 8/2004 | Unger |
| 6,884,407 B1 | 4/2005 | Unger |
| 6,943,692 B2 | 9/2005 | Castner et al. |
| 6,998,107 B2 | 2/2006 | Unger |
| 7,255,875 B2 | 8/2007 | Lanza et al. |
| 7,344,698 B2 | 3/2008 | Lanza et al. |
| 7,344,705 B2 | 3/2008 | Unger |
| 8,084,056 B2 * | 12/2011 | Hui et al. ............ 424/450 |
| 2004/0057991 A1 | 3/2004 | Hui et al. |
| 2005/0163716 A1 | 7/2005 | Unger et al. |
| 2008/0118435 A1 | 5/2008 | Unger |
| 2012/0027688 A1 | 2/2012 | Hui et al. |
| 2012/0128595 A1 | 5/2012 | Hui et al. |
| 2013/0022550 A1 | 1/2013 | Unger et al. |
| 2013/0309175 A1 | 11/2013 | Hui et al. |

FOREIGN PATENT DOCUMENTS

| | | |
|---|---|---|
| AU | 746067 B2 | 4/2002 |
| DE | 25 21 003 B1 | 8/1976 |
| DE | 38 03 972 A1 | 8/1989 |
| EP | 0 052 575 A2 | 5/1982 |
| EP | 0 077 752 A2 | 4/1983 |
| EP | 0 107 559 A1 | 5/1984 |
| EP | 0 216 730 A2 | 4/1987 |
| EP | 0 224 934 A2 | 6/1987 |
| EP | 0 231 091 A1 | 8/1987 |
| EP | 0 243 947 A1 | 11/1987 |
| EP | 0 272 091 A2 | 6/1988 |
| EP | 0 274 961 A1 | 7/1988 |
| EP | 0 314 764 A1 | 5/1989 |
| EP | 0 320 433 A2 | 6/1989 |
| EP | 0 324 938 A1 | 7/1989 |
| EP | 0 327 490 A1 | 8/1989 |
| EP | 0 338 971 A1 | 10/1989 |
| EP | 0 349 429 A2 | 1/1990 |
| EP | 0 357 164 A1 | 3/1990 |
| EP | 0 359 246 A2 | 3/1990 |
| EP | 357 163 A1 | 3/1990 |
| EP | 0 361 894 A2 | 4/1990 |
| EP | 0 382 619 A1 | 8/1990 |
| EP | 441 468 A2 | 8/1991 |
| EP | 0 458 745 A1 | 11/1991 |
| EP | 0 467 031 A1 | 1/1992 |
| EP | 0 554 213 A1 | 8/1993 |
| EP | 0 561 424 A1 | 9/1993 |
| EP | 0 562 641 A1 | 9/1993 |
| EP | 0 586 875 A1 | 3/1994 |
| EP | 0 614 656 A1 | 9/1994 |
| EP | 0 633 030 A1 | 1/1995 |
| EP | 0727225 A2 | 8/1996 |
| EP | 0 901 793 A1 | 3/1999 |
| EP | 0 957 942 A2 | 11/1999 |
| FR | 2 700 952 A1 | 8/1994 |
| GB | 1044680 A | 10/1966 |
| GB | 2193095 A | 2/1988 |
| JP | 62 286534 A | 12/1987 |
| JP | SHO 63-60943 | 3/1988 |
| JP | 63-277618 A | 11/1988 |
| JP | 2-149336 A | 6/1990 |
| JP | 7-505135 A | 6/1995 |
| JP | 8-151335 A | 6/1996 |
| JP | 8-511523 A | 12/1996 |
| WO | WO-80/02365 A1 | 11/1980 |
| WO | WO-82/01642 A1 | 5/1982 |
| WO | WO-84/02909 A1 | 8/1984 |
| WO | WO-85/01161 A1 | 3/1985 |
| WO | WO-85/02772 A1 | 7/1985 |
| WO | WO-86/00238 A1 | 1/1986 |
| WO | WO-86/01103 A1 | 2/1986 |
| WO | WO-89/05040 A1 | 6/1989 |
| WO | WO-89/10118 A1 | 11/1989 |
| WO | WO-90/1952 | 3/1990 |
| WO | WO-90/01952 A1 | 3/1990 |
| WO | WO-90/04384 A1 | 5/1990 |
| WO | WO-90/04943 A1 | 5/1990 |
| WO | WO-90/14846 A1 | 12/1990 |
| WO | WO-91/00086 A1 | 1/1991 |
| WO | WO-91/03267 A1 | 3/1991 |
| WO | WO-91/09629 A1 | 7/1991 |
| WO | WO-91/12823 A1 | 9/1991 |
| WO | WO-91/15244 A2 | 10/1991 |
| WO | WO-91/15753 A1 | 10/1991 |
| WO | WO-91/18612 A1 | 12/1991 |
| WO | WO-92/01675 A2 | 2/1992 |
| WO | WO-92/05806 A1 | 4/1992 |
| WO | WO-92/10166 A1 | 6/1992 |
| WO | WO-92/11873 A1 | 7/1992 |
| WO | WO-92/15284 A1 | 9/1992 |
| WO | WO-92/17212 A1 | 10/1992 |
| WO | WO-92/17213 A1 | 10/1992 |
| WO | WO-92/17436 A1 | 10/1992 |
| WO | WO-92/17514 A1 | 10/1992 |
| WO | WO-92/21382 A1 | 12/1992 |
| WO | WO-92/22247 A1 | 12/1992 |
| WO | WO-92/22249 A1 | 12/1992 |
| WO | WO-92/22298 A1 | 12/1992 |
| WO | WO-93/00933 A1 | 1/1993 |
| WO | WO-93/05819 A1 | 4/1993 |
| WO | WO-93/06869 A1 | 4/1993 |
| WO | WO-93/09762 A2 | 5/1993 |
| WO | WO-93/13802 A1 | 7/1993 |
| WO | WO-93/13809 A1 | 7/1993 |
| WO | WO-93/17718 A1 | 9/1993 |
| WO | WO-93/20802 A1 | 10/1993 |
| WO | WO-94/00110 A1 | 1/1994 |
| WO | WO-94/06477 A1 | 3/1994 |
| WO | WO-94/07539 A1 | 4/1994 |
| WO | WO-94/09829 A1 | 5/1994 |
| WO | WO-94/16739 A1 | 8/1994 |
| WO | WO-94/21301 A1 | 9/1994 |
| WO | WO-94/21302 A1 | 9/1994 |
| WO | WO-94/28780 A2 | 12/1994 |
| WO | WO-94/28797 A1 | 12/1994 |
| WO | WO-94/28873 A1 | 12/1994 |
| WO | WO-94/28874 A1 | 12/1994 |
| WO | WO-95/03835 A1 | 2/1995 |
| WO | WO-95/06518 A1 | 3/1995 |
| WO | WO-95/07072 A2 | 3/1995 |
| WO | WO-95/12387 A1 | 5/1995 |
| WO | WO-95/15118 A1 | 6/1995 |
| WO | WO-95/16467 A1 | 6/1995 |
| WO | WO-95/23615 A1 | 9/1995 |
| WO | WO-95/24184 A1 | 9/1995 |

(56) References Cited

FOREIGN PATENT DOCUMENTS

| | | |
|---|---|---|
| WO | WO-95/26205 A1 | 10/1995 |
| WO | WO-95/32005 A1 | 11/1995 |
| WO | WO-95/32006 A1 | 11/1995 |
| WO | WO-96/04018 A1 | 2/1996 |
| WO | WO-96/08234 A1 | 3/1996 |
| WO | WO-96/09793 A1 | 4/1996 |
| WO | WO-96/28090 A1 | 9/1996 |
| WO | WO-96/31196 A1 | 10/1996 |
| WO | WO-96/36286 A1 | 11/1996 |
| WO | WO-96/40281 A2 | 12/1996 |
| WO | WO-96/40285 A1 | 12/1996 |
| WO | WO-97/00638 A2 | 1/1997 |
| WO | WO-97/40679 A1 | 11/1997 |
| WO | WO-97/40858 A1 | 11/1997 |
| WO | WO-97/48337 A1 | 12/1997 |
| WO | WO-98/00172 A2 | 1/1998 |
| WO | WO-98/04292 A2 | 2/1998 |
| WO | WO-98/09600 A2 | 3/1998 |
| WO | WO-98/10798 A1 | 3/1998 |
| WO | WO-98/10799 A1 | 3/1998 |
| WO | WO-98/17324 A2 | 4/1998 |
| WO | WO-98/18495 A2 | 5/1998 |
| WO | WO-98/18498 A2 | 5/1998 |
| WO | WO-98/18500 A2 | 5/1998 |
| WO | WO-98/18501 A2 | 5/1998 |
| WO | WO-98/42384 A1 | 10/1998 |
| WO | WO-98/47487 A1 | 10/1998 |
| WO | WO-98/50040 A1 | 11/1998 |
| WO | WO-98/50041 A1 | 11/1998 |
| WO | WO-98/51284 A1 | 11/1998 |
| WO | WO-99/08714 | 2/1999 |
| WO | WO-99/13919 A1 | 3/1999 |
| WO | WO-99/30620 | 6/1999 |
| WO | WO-99/36104 A2 | 7/1999 |
| WO | WO-99/39738 A1 | 8/1999 |
| WO | WO-00/45856 A2 | 8/2000 |
| WO | WO-01/15742 A1 | 3/2001 |
| WO | WO 2004/030617 A1 | 4/2004 |

OTHER PUBLICATIONS

[No Author Listed] EMEA Scientific discussion relating to Sonovue. Updated until Oct. 1, 2004. 1 page.
[No Author Listed] Pages from DuPont website relating to Freon. Last accessed online at http://www.dupont.com/msds/40_37_2011fr.html on Feb. 15, 2002. 5 pages.
A G. Belykh, Farmakol Toksikol. (MOSC), vol. 44(3), pp. 322-326 (1981) (abstract).
Acoustic Imaging; AI5200; Convex Curved Linear Array Ultrasound Transducers Operator's Mnaual, Nov. 20, 1989, 4700-0003-1C, p. 4.
Anderson et al., "Manganese (III) Complexes in Oxidative Decarboxylation of Acids", J. Am. Chem. Soc., vol. 92, No. 8, pp. 2450-2460 (1970).
Arai et al., Transpulmonary passage of Aerosomes®, a pressure stable, lipid based echocardiographic contrast agent: studies in pigs. J Am Coll Cardiol. 1994:23-25A. Abstract only.
Aronberg, "Techniques", Computed Body Tomography, Lee, et al., eds., Raven Press, New York, Chapter 2, pp. 9-36 (1988).
Bangham et al., "Diffusion or Univalent Ions across the Lamellae of Swollen Phospholipids", J. Mol. Biol., 1965, 13:238-252.
Barenholz et al., Handbook of Nonmedical Application of Liposomes. CRC Press, 1996.
Barnhart et al., "Characteristics of ALBUNEX.TM.: Air-Filled Microspheres for Echocardiography Contrast Enhancement," Investigative Radiology, 25:S162-164 (Sep. 1990).
Bedu-Addo, F.K., et al., "Effects of polyethyleneglycol chain length and phospholipids acyl chain composition on the interaction of polyethyleneglycol-phospholipid conjugants with phospholipids: implications in liposomal drug delivery," Pharm. Res., May 1996, 13(5), 710-717.
Belsito, S., et al., "Sterically stabilized liposomes of DPPC/DPPE-PEG 2000—A spin label ESR & spectrophotometric study," Biophysical Chem., May 10, 1998, 75(1), 33-43.

Blomley et al., "Microbubble contrast agents: a new era in ultrasound"; Clinical Review XP008001399, BMJ, vol. 322, pp. 1222-1225 (May 19, 2001).
Botvinick, Stress imaging: current clinical options for the diagnosis, localization, and evaluation of coronary artery disease. Contemporary Issues Cardiol. Sep. 1995;79(5):1025-57.
Brochure, Experience, SonicatorTM. Heat Systems-Ultrasonics, Inc. (1987).
Brown and Langer, Annual Review Medicine, 1988, 39:221 29, Annual Review, Inc., "Transdermal Delivery of Drugs", pp. 221-229.
Burn et al., Stress echocardiography. Q J med. 1995;88:755-61.
Carson et al., "Ultrasound Power and Intensitites Produced by Diagnostic Ultrasound Equipment", Ultrasound in Med. & Biol., vol. 3, pp. 341-350 (1978).
Chang, "Semipermeable Aqueous Microcapsules", Canadian J. of Phys. and Pharm., 1966, vol. 44, pp. 115-128 (1978).
Chang, "Semipermeable Microcapsules", Science, 1964, 146, 524-525.
Chapman et al., "Biomembrane Phase Transitions", J. Biol. Chem., vol. 249, pp. 2512-2521(1974).
Chapman, "Physiochemical Properties of Phospholipids and Lipid-Water Systems", Liposome Technology, Gregoriadis, G., ed., Chapter 1, vol. 1, pp. 1-18 (CRC Press, Boca Raton, FL, 1984).
Cheng et al., "The Production and Evaluation of Contrast-Carrying Liposomes Made with an Automatic High Pressure System", Investigative Radiology, vol. 22, No. 1, pp. 47-55 (1987).
Chortkoff et al., "Pharmacokinetics Do Not Explain the Absence of an Anesthetic Effect of Perfluoropropane or Perfluoropentane." Anesth. Analg., 79, pp. 234-237, 1994.
Crowe et al., "Preservation of Freeze-Dried Liposomes by Trehalose", Archives of Biochemistry and Biophysics, vol. 242, pp. 240-247 (1985).
Crowe et al., "Preservation of Structural and Functional Activity in Lyophilized Sarcoplasmic Reticulum", Archives of Biochemistry and Biophysics, vol. 220, pp. 477-484 (1983).
De Jong et al., New ultrasound contrast agents and technological innovations. Ultrasonics. Jun. 1996;34(2-5):587-90.
Deamer et al., "Permeability of Lipid Bilayers to Water and Ionic Solutes", Chemistry and Physics of Lipids, vol. 40, pp. 167-188 (1986).
Deamer, D.W., "Preparation of solvent vaporization liposomes," Liposome Techn., 1984, vol. 1, Chap. 3, 29-35.
Deasy, Microencapsulation and Related Drug Processes, vol. 20, Chs. 9 and 10, pp. 195-239 (1983) (Marcel Dekker, Inc., NY).
deGier et al., "Relations Between Liposomes and Biomembranes", Annals of New York Academy of Sciences, vol. 308, pp. 85-99 (1978).
Desir et al., "Assessment of regional myocardial perfusion with myocardial contrast echocardiography in a canine model of varying degrees of coronary stenosis", American Heart Journal, vol. 127, No. 1, pp. 56-63 (Jan. 1994).
Ding et al., Chung Kuo Yao Li Hsueh Pao, Sep. 1989; 10(5):473-5 (Abstract only).
Dittrich, "Cardiac Muscle lschemia and Infarction", The Second Annual International Symposium on Contrast Agents in Diagnostic Ultrasound, Atlantic City, NJ (May 7, 1996) (abstract).
Dorland's Illustrated Medical Dictionary, p. 946, 27th ed. (W.B. Saunders Company, Philadelphia 1988).
Feigenbaum et al., Circulation, "Identification of Ultrasound Echoes from the Left Ventricle by Use of Intracardiac Injections of Indocyanine Green", vol. XL1, pp. 615-621 (Apr. 1970).
Feinstein et al., "Two-Dimensional Contrast Echocardiography. I. In Vitro Development and Quantitative Analysis of Echo Contrast Agents", JACC, vol. 3, No. 1, pp. 14-20 (1984).
Feinstein, Steven B., "Myocardial Perfusion Imaging: Contrast Echocardiography Today and Tomorrow," Journal of the American College of Cardiology, 8(1):251-253 (1986).
Feigner et al., "Lipofection: A highly efficient, lipid-mediated DNA-transfection procedure", Proc. Natl. Acad. Sci., vol. 84, pp. 7413-7417 (1987).
Fitzpatrick, et al., "Metal Ion Catalyzed Decarboxylation: Kinetics and Mechanism of the Oxidative Decarboxylation of Copper (II)

(56) References Cited

OTHER PUBLICATIONS

Complexes of Aminomalonic Acid in Aqueous Solution", Inorganic Chemistry, vol. 13, No. 3, pp. 568-574 (1974).

Frezard, et al., "Fluorinated Phospholipid-Based Vesicles as Potential Drug Carriers: Encapsulation/Sustaining of Drugs and Stability in Human Serum", Art, Cells, Blood Subs., and Immob. Biotech., 22(4), pp. 1403-1408 (1994).

Frezard, et al., "Permeability and stability in buffer and in human serum of fluorinated phospholipid-based liposomes", Biochimica et Biophysica Acta, 1192, pp. 61-70 (1994).

Fritzsch et al., "Preclinical and Clinical Results with an Ultrasonic Contrast Agent", Inv. Rad., vol. 23, pp. S302-S305, Sep. 1988.

Fukuda et al., "Polymer-Encased Vesicles Derived from Dioctadecyldimethylammonium Methacrylate", J. Am. Chem. Soc., vol. 108, pp. 2321-2327 (1986).

Gabizon et al., "Liposome formulations with prolonged circulation time in blood and enhanced uptake by tumors", Proc. Natl. Acad. Sci., vol. 85, pp. 6949-6953 (1988).

Gaentzler et al., "Perfluoroalkylated Phosphocholines. Improved Synthesis, Surface Activity, Fluorocarbon Emulsifying Capability and Biological Properties", New Journal of Chemistry 1993, 17(5), 337-344.

Galjee, Biosis #91:493622, 1991.

Gardner et al., "A Survey of Intraocular Gas Use in North America", Arch. Ophthalmol., vol. 106, pp. 1188-1189, Sep. 1988.

Garelli, et al., "Incorporation of new amphiphilic perfluoroalkylated bipyridine platinum and palladium complexes into liposomes: stability and.." Biochimica et Biophysica Acta, vol. 1127, pp. 41-48 (1992).

Goldberg, et al., "Ultrasound contrast agents: a review," Ultrasound in Med. & Biol., 1994, 20(4), 319-333.

Gramiak et al., "Detection of Intracardiac Blood Flow by Pulsed Echo-Ranging", Radiology, vol. 100, pp. 415-418 (1971).

Gregodiadis, G., et al. (Eds.), "Liposome technology: preparation of liposomes," and Deamer: "Preparation of solvent vaporization liposomes,"CRC Press, Inc., 1984, CRC Press, Inc., XP002101586, vol. 1, 31-35.

Gregoriadis, G. (Ed.), Liposome technology: preparation of lipsomes, CRC Press, 1994, vol. 1, 7-13.

Gregoriadis, G., ed., Liposome Technology, vol. I, pp. 29-35, 51-65 and 79-107, CRC Press, Boca Raton, FL 1984.

Gross, U. et al., "Phosholipid vesiculated fluorocarbons promising trend in blood substitutes" Biomat., Art. Cells & Immob. Biotech., 1992, vol. 20, (2-4) pp. 831-833.

Gunstone et al., The Lipid Handbook, 2nd Edition. Chapman and Hall Chemical Data Base, 1992.

Gutknecht et al., "Diffusion of carbon dioxide through lipid bilayer membranes. Effects of carbonic anhydrase, bicarbonate, and unstirred layers", Chemical Abstracts, vol. 87, 34772q, p. 136 (1977).

H. Meessen, ed., Microcirculation, Springer-Verlag, Berlin Heidelberg, New York, p. 44 (1997) (German language only).

Handbook of Pharmaceutical Excipients, American Pharmaceutical Association, Washington, D.C. and The Pharmaceutical Society of Great Britain, London, England, pp. 181-183 (1986).

Hansrani, et al., "The preparation and properties of sterile intravenous emulsion," J. Parent. Sci. Tech., 1983, 37(4), 145-150.

Hautanen, A. et al., "Effects of Modifications of the RGD sequence and its Context on Recognition by the Fibronectin Receptor", J. Biol. Chem., 1989, 264(3), 1437-1442.

Hayat et al., Effects of left bundle-branch block on cardiac structure, function, perfusion, and perfusion reserve: implications for myocardial contrast echocardiography versus radionuclide perfusion imaging for the detection of coronary artery disease. Circulation. Apr. 8, 2008;117(14):1832-41. Epub Mar. 31, 2008.

Hope et al., "Generation of Multilamellar and Unilamellar Phospholipid Vesicles", Chemistry and Physics of Lipids, vol. 40, pp. 89-107 (1986).

Hope et al., "Production of large unilamellar vesicles by a rapid extrusion procedure. Characterization of size distribution, trapped volume, and ability to maintain a membrane potential", Biochimica et Biophysica Acta, vol. 812, pp. 55-65 (1985).

Hug et al., "Liposomes for the Transformation of Eukaryotic Cells", Biochimica et Biophysica Acta, 1991, 1097:1-17.

Hynynen et al., "The Usefulness of a Contrast Agent and Gradient-Recalled Acquisition in a Steady-State Imaging Sequence for Magnetic Resonance Imaging-Guided Noninvasive Ultrasound Surgery," Investigative Radiology, vol. 29, pp. 897-903 (Oct. 1994).

Isele, et al., "Large-scale production of liposome containing monomeric zinc phthalocyanine by controlled dilution of organic solvents," J. Pharm. Sci., 1994, 83(11), 1608-1616.

J. Vion-Dury et al., J. Pharmacol. Exper. Therm., vol. 250(3), pp. 1113-1118 (1989) (abstract).

Jackson et al., "Effect of ultrasound therapy on the repair of Achilles tendon injuries in rats." Medicine and Science in Sports and Exercise, vol. 23, No. 2, pp. 171-176, 1991.

Jacobs, "Intraocular gas measurement using A-scan ultrasound", Current Eye Research, vol. 5, No. 8, pp. 575-578 (1986).

Jain, et al., "Facilitated Transport", Introduction to Biological Membranes, Ch. 9, pp. 192-231 (J. Wiley and Sons, N.Y. 1980).

Kaul, Myocardial contrast echocardiography in coronary artery disease: potential applications using venous injections of contrast. Am J Cardiol. Apr. 13, 1995;75(11):61D-68D.

Kawai et al., "New Procedure for DNA Transfection with Polycation and Dimethyl Sulfoxide", Molecular and Cellular Biology, vol. 4, No. 6, pp. 1172-1174 (1984).

Kazuo, M., et al., "Prolonged circulation time in vivo of large unilamellar liposomes composed of distearoyl phosphatidylcholine and cholesterol containing amphipathic poly *ethylene glycol)," Biochimica et Biophysica Acta, 1992, 1128, 44-49.

Keller et al., "Successful Left Ventricular Opacification Following Peripheral Venous Injection of Sonicated Contrast Agent: An Experimental Evaluation", LV Contrast Echocardiography, vol. 114, No. 3, pp. 570-575 (1987).

Keller et al., "The Behavior of Sonicated Albumin Microbubbles Within the Microcirculation: A Basis for Their Use During Myocardial Contrast Echocardiography", Circulation Res., vol. 65, No. 2, pp. 458-467 (Aug. 1989).

Kinsler, et al., Fundamentals of Acoustics, third ed., pp. 228-331 (1982).

Kost et al., Polymers in Medicine II: Biomedical and Pharmaceutical Applications, "Ultrasonic Modulated Drug Delivery Systems", Chiellini et al., eds., (Plenum Press, New York and London), pp. 387-396 (1985).

Kuo et al., "Metallocene Antitumor Agents. Solution and Solid-State Molybdenocene Coordination..", J. Am. Chem. Soc., vol. 113, No. 24, pp. 9027-9045 (1991).

Lejbkowicz et al., "The response of normal and malignant cells to ultrasound in vitro." Database BIOSIS, No. 1993:95122245 (abstract only).

Levene et al., "Characterization of AlbunexTM," J. Acoust. Soc. Am., 87 (Suppl.1):569-70 (Spring 1990).

Lincoff et al., "Intravitreal Expansion of Perfluorocarbon Bubbles", Arch. Ophthalmol., vol. 98, p. 1646, Sep. 1980.

Lincoff et al., "Intravitreal Longevity of Three Perfluorocarbon Gases", Arch. Ophthalmol., vol. 98, pp. 1610-1611, Sep. 1980.

Lincoff et al., "Perfluoro-n-butane: A Gas for Maximum Duration Retinal Tamponade," Arch Ophthalmology, 101:460-462 (1983).

Lincoff et al., "The Perfluorocarbon Gases in the Treatment of Retinal Detachment", Ophthalmology, vol. 90, No. 5, pp. 546-551, May 1983.

Lindner et al., "Myocardial Perfusion Characteristics and Hemodynamic Profile of MRX-115, a Venous Echocardiographic Contrast Agent, During Acute Myocardial Infarction," J. Am. Soc. of Echocardiography, vol. 11, No. 1, pp. 36-46 (Jan. 1998).

Liposome Technology, Gregoriadis, G., ed., vol. I, pp. 1-18, 30-35, 51-65 and 79-107 (CRC Press Inc., Boca Raton, FL, (1984).

M. Ostro, "Liposomes", Marcel Dekker, New York, pp. 102-103 (1983).

M. R. Zalutsky et al., Invest. Radiol., vol. 22(2), pp. 141-147 (1987) (abstract).

(56) References Cited

OTHER PUBLICATIONS

MacDonald, Mammalian Cell Biotechnology: A Practical Approach, M. Butler, ed., (Oxford University Press, New York), Chapter 4, pp. 57-70 (1991).
MacNaughton et al., "Effects of Gaseous Anaesthetics and Inert Gases on the Phase Transition in Smectic Mesophases of Dipalmitoyl Phosphatidylcholine", Biochimica et Biophysica Acta, vol. 597, pp. 193-198 (1980).
Madden et al., "The accumulation of drugs within large unilamellar vesicles exhibiting a proton gradient: a survey", Chemistry and Physics of Lipids, vol. 53, pp. 37-46 (1990).
Mann et al., "Formation of Iron Oxides in Unilamellar Vesicles", Journal of Colloid and Interface Science, vol. 122, No. 2, pp. 326-335 (1988).
Marsh et al., Handbook of Lipid Bilayers. CRC Press, 1990.
Marsh, CRC Handbook of Lipid Bilayers (CRC Press, Boca Raton, FL 1990) pp. 139-141.
Maruyama, K., et al., "Prolonged circulation time in vivo of large unilamellar liposomes composed of distearoyl phosphatidylcholine and cholesterol containing amphipathic ply(ethylene glycol)," Biochimica et Biophysica Acta, 1992, 1128, 44-49.
Mathews et al., Biochemistry. Benjamin/Cummings Publishing Co., 1990:332-3.
Mathiowitz et al., "Photochemical Rupture of Microcapsules: A Model System", Journal of Applied Polymer Science, vol. 26, pp. 809-822 (1981).
Mathiowitz et al., "Polyanhydride Microspheres as Drug Carriers. II. Microencapsulation by Solvent Removal", Journal of Applied Polymer Science, vol. 35, pp. 755-774 (1988).
Mattrey et al., "Perfluorochemicals as US Contrast Agents for Tumor Imaging and Hepatosplenography: Preliminary Clinical Results", Radiology, vol. 163, No. 2, pp. 339-343 (1987).
Mattrey et al., "Perfluoroctylbromide: A Liver/Spleen-Specific and Tumor-Imaging Ultrasound Contrast Material", Radiology, vol. 145, pp. 759-762 (1982).
Mattrey et al., Gas Emulsions as Ultrasound Contrast Agents; Preliminary Results in Rabbits and Dogs, Investigative Radiology, vol. 29, Jun. Supp. 2, pp. S139-S141, 1994.
Maxwell, "Therapeutic Ultrasound: Its Effects on the Cellular and Molecular Mechanisms of Inflammation and Repair." Physiotherapy, vol. 78, No. 6, pp. 421-426, Jun. 1992.
May et al., "Cationic Liposomes Enable Bovine Herpesvirus Type 2 DNA to Infect Cells", Acta virol., 1991, 35:107.
Mayer et al., "Vesicles of Variable Size Produced by a Rapid Extrusion Procedure", Biochimica et Biophysica Acta, vol. 858, pp. 161-168 (1986).
Mayhew et al., "Characterization of Liposomes Prepared Using a Microemulsifier", Biochimica et Biophysica Acta, vol. 775, pp. 169-174 (1984).
Mayhew et al., "High-Pressure Continuous-Flow System for Drug Entrapment in Liposomes", Methods in Enzymology, vol. 149, pp. 64-77 (1987).
McAvoy et al., IEEE Engineering, Ultrasonics Symposium Proceedings, vol. 2, pp. 677-1248 (1989) (abstract).
Meessen, H. (ed.), Microcirculation, Springer-Verlag, Berlin Heidelberg, New York, 1997, 44.
Meltzer et al., Transmission of Ultrasonic Contrast Through the Lungs, Ultrasound in Med. & Biol., vol. 7, No. 4, 377-384, 1981.
Miller et al., "Physiochemical Approaches to the Mode of Action of General Anesthetics," J. Amer. Soc. Anesthesiologists, 36(4):339-351 (1972).
Miller, D.L., "Ultrasonic Detection of Resonant Cavitation Bubbles in a Flow Tube by Their Second-Harmonic Emissions", Ultrasonics, Sep. 1981, 217-224.
Moseley, et al., Microbubbles: A Novel MR Susceptibility Contrast Agent, abstract, 1991 Napa, California Meeting of the Society for Magnetic Resonance in Medicine.
Muhlradt et al., "Vitamin B6 Analogs: An Improved Synthesis of 5-Deoxypyridoxal", New Compounds, vol. 10, pp. 129-130 (1967).

Nayar et al., "Generation of Large Unilamellar Vesicles From Long-chain Saturated Phosphatidylcholines by Extrusion Techinque", Biochimica et Biophysica Acta, vol. 986, pp. 200-206 (1989).
New, R.R.C. (Ed.), "Liposomes a practical approach," IRL Press, 1990, 62-77.
Nikolova, A., et al., "Effect of grafted PEG-2000 on the size and permeability of vesicles," Biochim Biophys Acta, Nov. 22, 1996, 1304(2), 120-128.
Nomura et al., "US Contrast Enhancement of Hepatic Tumor with Helium Gas Microbubbles: A Preliminary Report", Jpn. J. Med. Ultrasonics, vol. 18, No. 5 (1991) (Japanese with English language abstract).
O'Keefe et al., Comparison of stress echocardiography and stress myocardial perfusion scintigraphy for diagnosing coronary artery disease and assessing its severity. Am J Cardiol. Apr. 13, 1995;75(11):25D-34D.
Ohki, et al., "Short & long range calcium-induced lateral phase separations in ternary mixtures of phosphatidic acid phosphatidylcholine and phosphatidylethanolamine," Chem. & Physics of Lipids, 1989, 50(2), 109-118.
Ophir et al., "Contrast Agents in Diagnostic Ultrasound", Ultrasound in Med. & Biol., vol. 15, No. 4, pp. 319-333 (1989).
Otis et al., Contrast-enhanced transcranial imaging. Results of an American phase-two study. Stroke. Feb. 1995;26(2):203-9.
P.N.T. Wells, "Pulse-Echo Methods", Biomedical Ultrasonics, Academic Press, pp. 209-220 (1977).
Pantely, "Intravenous Contrast Echocardiography—Tissue Imaging & Quantification of Coronary Blood Flow", The Second Annual International Symposium on Contrast Agents in Diagnostic Ultrasound, Atlantic City, NJ (May 7, 1996) (abstract).
Papahadjopoulos et al., Sterically stabilized liposomes:improvements in pharmacokinetics and antitumor therapeutic efficacy. Proc Natl Acad Sci U S A. Dec. 15, 1991;88(24):11460-4.
Pietersen, "A New Warning System for Fires of Electrical Origin", CERN European Organization for Nuclear Research, Health and Safety Division, pp. 1-5 (Mar. 1977).
Porter, et al., "Multifold Sonicated Dilutions of Albumin with Fifty Percent Dextrose Improve Left Ventricular Contrast Videointensity After Intravenous Injection in Human Beings", Journal of the American Society of Echocardiography, vol. 7, No. 5,pp. 465-471, Sep.-Oct. 1994.
Porter, et al., "Noninvasive Identification of Acute Myocardial lschemia and Reperfusion With Contrast Ultrasound Using Intravenous Perfluorpropane-Exposed Sonicated Dextrose Albumin", Journal of the American College of Cardiology, vol. 26, No. 1, pp. 33-40; 1995.
Porter, et al., "Thrombolytic enhancement with perfluorocarbon-exposed sonicated dextrose albumin microbubbles", vol. 132, No. 5, American Heart Journal, pp. 964-968, Nov. 1996.
Porter, et al., "Visually Discernible Myocardial Echocardiographic Contrast After Intravenous Injection of Sonicated Dextrose Albumin Microbubbles Containing High Molecular Weight, Less Soluble Gases", Journal of the American College of Cardiology,vol. 25, No. 2, pp. 509-515, Feb. 1995.
Poznansky et al., "Biological Approaches to the Controlled Delivery of Drugs: A Critical Review", Pharmacol. Rev., vol. 36, No. 4, pp. 277-336 (1984).
PR Newswire, Apr. 1, 1986.
Regen et al., "Polymerized Phosphatidylcholine Vesicles. Synthesis and Characterization," J. Am. Chem. Soc., vol. 104, No. 3, pp. 191-195 (1982).
Regen et al., Polymerized phospatidylcholine vesicles. Synthesis and characterization. J Am Chem Soc. 1982;104:791-5.
Regen, "Polymerized Vesicles", J. Am. Chem. Soc., vol. 102, pp. 6638-6640 (1980).
Remington's Pharmaceutical Sciences, John Hoover, managing ed., Mack Publishing Company, Easton, PA, pp. 295-298; 736; 1242-1244 (1975).
Riess, J.G., "Fluorine in our arteries," New J.Chem., XP-000990897, 1995, 19, 891-909 (English abstract).
Riess, J.G., "Introducing a new element-fluorine-into the liposomal membrane", Liposome Res., 1995, XP-000525914, 5(3), 413-430.

(56) References Cited

OTHER PUBLICATIONS

Ring et al., Clinical Weekly, 52, pp. 595-598 (1974) (English abstract).
Robinson, et al., F.J. Fry, ed., Ultrasound: Its Applications in Medicine and Biology, Elsevier Scientific Publishing Company, vol. 3, Chap. XI, pp. 593-596 (1978).
Rose, A. and Rose, E., "The Condensed Chemical Dictionary", Reinhold Publishing, New York, pp. 728 and 743 (1966).
Sankaram et al., "Cholesterol-Induced Fluid-Phase Immiscibility in Membranes", Proc. Natl. Acad. Sci., vol. 88, pp. 8686-8690 (1991).
Santaella, C. et al., "Emulsification of Fluorocarbons Using Perfluoroalkylated Glycerophosphocholines as Surfactants or Co-Surfactants", New J. Chem., 1992, 16(3), 399-404.
Santaella, et al., "Extended In Vivo Blood Circulation Time of Fluorinated Liposomes", FEBS 13463, vol. 336, No. 3, pp. 481-484 (1993).
Sato et al., "Recent Aspects in the Use of Liposomes in Biotechnology and Medicine", Prog. Lipid Res., vol. 31, No. 4, pp. 345-372 (1992).
Scarpa et al., "Cation Permeability of Liposomes as a Function of the Chemical Composition of the Lipid Bilayers", Biochimica et Biophysica Acta, vol. 241, pp. 789-797 (1971).
Schutt et al., "Osmotically Stabilized Microbubble Sonographic Contrast Agents", Acad. Radiol., vol. 3, Suppl. 2, pp. 5188-5190 (Aug. 1996).
Scientific Apparatus Catalog 92/93 (VWR Scientific, 1991), "Syringes", pp. 1511-1513; "Filtration, Syringe Filters", pp. 766-768; "Filtration, Membranes", pp. 750-753; "Filtration, Filter Holders", p. 744.
Seibyl, Biois #94:339104, 1994.
Sekins et al., "Lung Cancer Hyperthermia via Ultrasound and PFC Liquids", Published in Proceedings of 5th International Symposium on Hyperthermic Oncology, Kyoto, Japan, (3 pages) (Aug. 29-Sep. 3, 1998).
Senior et al., "Influence of surface hydrophilicity of liposomes on their interaction with plasma protein and clearance from the circulation: studies with poly(ethylene glycol)-coated vesicles." Biochimica et Biophysica Acta. 1991. 1062. pp. 77-82.
Senior et al., RAMP-1 and RAMP-2 Investigators. Detection of coronary artery disease with perfusion stress echocardiography using a novel ultrasound imaging agent: two Phase 3 international trials in comparison with radionuclide perfusion imaging. Eur J Echocardiogr. Jan. 2009;10(1):26-35.
Senior, Imagify (perflubutane polymer microspheres) injectable suspension for the assessment of coronary artery disease. Expert Rev Cardiovasc Ther. May 2007;5(3):413-21.
Sharma et al., "Emulsification Methods for Perfluorochemicals." Drug Development and Industrial Pharmacy, 14 (15-17), pp. 2371-2376 (1988).
Shiina et al., "Hyperthermia by Low-frequency Synthesized Ultrasound", IEEE Engineering, pp. 879-880, vol. 2 (1988) (abstract).
Shinoda, K. et al., "Colloidal Surfactants; Some Physiochemical Properties", Chapter 1, pp. 1-96, Academic Press, New York, 1963.
Sibernagl, D., Pocket Atlas of Physiology ,Georg Thieme Verlag, Stuttgart New York, 1983, 156-157 (German language only). Kinsler, et al., Fundamentals of Acoustics, third ed., pp. 228-331 (1982).
Sigel, H., ed., Metal Ions in Biological Systems: Antibiotics and Their Complexes, vol. 19 (Marcel Dekker, N.Y. 1985).
Simons et al., "Antisense c-myb oligonucleotides inhibit intimal arterial smooth muscle cell accumulation in vivo", Nature, vol. 359, pp. 67-70 (1992).
Sinkula et al., "Rationale for Design of Biologically Reversible Drug Derivatives: Prodrugs", J. Pharm. Sci. 1975, 64:181-210.
Sole-Violan, L., "Partition Coefficients of Mixed Fluorocarbon-Hydrocarbon Compounds Between Fluorocarbons and Hexadecane. Relevance of Fluorocarbon Emulsion Stabilization", New J. Chem., 1993, 17(8,9), 581-583.
Sonne et al., Left ventricular opacification after intravenous injection of Albunex. The effect of different administration procedures. Int J Card Imaging. 1995 Mar;11(1):47-53.
Srinivasan, et al., "Characterization of Binding Sites, Extent of Binding, and Drug Interactions of Oligonucleotides with albumin", Antisense Research and Development, vol. 5, pp. 131-139, 1995.
Stelmashok et al., Koordinatsinonnaya Khimiya, vol. 3, No. 4, pp. 524-557 (1977) (Russian and English and language versions).
Sutherland et al., "Color Doppler Myocardial Imaging: A New Technique for the Assessment of Myocardial Function", J. Am. Soc. of Echocardiogr, 1994, 7(5), 441-458.
Swanson et al., "Enhancement Agents for Ultrasound: Fundamentals", Pharmaceuticals in Medical Imaging, Chapter 22, pp. 682-687 (1990).
Szoka et al., Procedure for preparation of liposomes with large internal aqueous space and high capture by reverse-phase evaporation. Proc. Natl. Acad. Sci., vol. 75, No. 9, pp. 4194-4198 (1978).
Szoka, et al., "Comparative properties and methods of preparation of liqid vesicles (Liposomes)," Ann. Rev. Biophys. Bioeng., 1980,9, 467-508.
Takeuchi et al., "Enhanced Visualization of Intravascular Thrombus with the Use of a Thrombus Targeting Ultrasound Contrast Agent (MRX408): Evidence From in Vivo Experimental Echocardiographic Studies", The Journal of the American College of Cardiology, vol. 31, No. 2, Suppl. A, p. 57A, Abstract XP-000952675, Feb. 1998 and 47th Annual Scientific Session of American College of Cardiology, Atlanta, GA, Mar. 29, 1998-Apr. 1, 1998.
Talsma, et al., "Liposomes as drug delivery systems, part I, Preparation," Pharmaceutical Technology, Oct. 1992, 96-106.
Ten Cate et al., "Two-Dimensional Contrast Echocardiography. II: Transpulmonary Studies", JACC, vol. 3, No. 1, pp. 21-27 (1984).
Ter-Pogossian, Physical principles and instrumentation. Computed Body Tomography. Lee et al., eds., Raven Press, New York. Chapter 1. pp. 1-7 (1988).
Thanassi, "Aminomalonic Acid. Spontaneous Decarboxylation and Reaction with 5-Deoxypyridoxal", Biochemistry 1970, 9(3), 525-532.
Thompson, Larry, "At Age 2, Gene Therapy Enters a Growth Phase", Science 1992, 258:744-746.
Tilcock et al., "99mTc-labeling of Lipid Vesicles Containing the Lipophilic Chelator PE-DTTA: Effect of Tin-to-chelate Ratio, Chelate Content and Surface Polymer on Labeling Efficiency and Biodistribution Behavior." 2211b Nuclear Medicine and Biology, 21, No. 1, pp. 89-96, 1994.
Tilcock et al., "Liposomal Gd-DTPA: Preparation and Characterization of Relaxivity", Radiology, vol. 171, No. 1, pp. 77-80 (1989).
Tilcock et al., "PEG-coated Lipid Vesicles with Encapsulated Technetium-99m as Blood Pool Agents for Nuclear Medicine", 2211b Nuclear Medicine and Biology, 1994, 21(2), 165-170.
Trevino, L, et al., "Incorporation of a perfluoroalkylalkane (rfrh) into the phospholipid bilayer of dmpc liposomes results in greater encapsulation stability", Journal of Liposome Research, 1994, vol. 4 (2) pp. 1017-1028.
Trubetskoy et al., "Cationic liposomes enhance targeted delivery and expression of exogenous DNA . . . ", Biochimica et Biophysica Acta, vol. 1131, pp. 311-313 (1992).
Tsutsui et al., Comparison of low-mechanical index pulse sequence schemes for detecting myocardial perfusion abnormalities during vasodilator stress echocardiography. AmJ Cardiol. Mar. 1, 2005;95(5):565-70.
Tuncay et al., "Expression of Genes Associated with Tissue Remodeling Upon Ultrasound Perturbation in the Gingival Fibroblast." Journal of Dental Research, vol. 75, p. 143, 1996 (abstract only).
Uemura, Biosis #80: 105491, 1979.
Uemura, Embase, #79180131, 1979.
Ulendorf, "Physics of Ultrasound Contrast Imaging: Scattering in the Linear Range", IEEE Transactions on Ultrasonics, Ferrolectrics, and Frequency Control, 1994, 41(1), 70-79.
Umemura et al., "Studies on Sonodynamic Cancer Therapy", IEEE, 0/7803-0785, pp. 354- 355 (1992).
Unger et al., "Hepatic Metastases: Liposomal Gd-DTPA-enhanced MR Imaging", Radiology, vol. 171, No. 1, pp. 81-85 (1989).

(56) References Cited

OTHER PUBLICATIONS

Unger et al., "Liposomal Mr Contrast Agents", J. Liposome Research, 4(2), pp. 811-834 (1994).
Unger, et al., "Gas filled lipid bilayers as imaging contrast agents," J. Liposome Res., 1994, 4(2), 861-874.
Unger, et al., "Gas-filled lipid bilayers as ultrasound contrast agent," Invest. Radiol., 1994, 29S2, S134-S136.
Unger, et al., "In Vitro Studies of a New Thrombus-Specific Ultrasound Contrast Agent", American Journal of Cardiology, vol. 81, No. 12, Suppl. A, pp. 58G-61G, XP-002087505, Jun. 12, 1998 and Symposium: Ninth International Congress on Echocardiography: Clinical Cardiology, 1997.
Villanueva et al., "Characterization of Spatial Patterns of Flow Within the Reperfused Myocardium by Myocardial Contrast Echocardiography", Circulation, vol. 88, No. 6, pp. 2596-2606 (Dec. 1993).
Violante et al., "Particulate Suspensions as Ultrasonic Contrast Agents for Liver and Spleen", Inv. Rad., vol. 23, pp. S294-S297, Sep. 1988.
Wade et al., Handbook of Pharmaceutical Excipients, 2nd Ed. American Pharmaceutical Association, Washington. 1994.
Wang, et al., "Low Intensity Ultrasound Treatment Increases Strength in a Rat Femoral Fracture Model", Journal of Orthopaedic Research, 1994, 12(1), 40-47.
Wei et al., "Quantification of Myocardial Blood Flow With Ultrasound-Induced Destruction of Microbubbles Administered as a Constant Venous Infusion," Circulation, vol. 97, pp. 473-483 (1998).
Wheatley et al., "Contrast Agents for Diagnostic Ultrasound: Development and Evaluation of Polymer-Coated Microbubbles," Biomaterials, 11:713-717 (1990).
Williams, "Human Gene Therapy: Searching for Better Vectors", ASM News [American Society for Microbiology] vol. 58, pp. 67-69 (1992).
Wolf, A., et al., "The effect of lysophosphatidylcholine on coronary and renal circulation in the rabbit," Lipids, 1991, 26(3), 223-226 (Abstract, 1 page).
Woodle et al., "Versatility in lipid compositions showing prolonged circulation . . . ", Biochimica et Biophysica Acta 1992, 1105:193-200.
Wu, Y., et al., "Binding and lysing of blood clots using MRX-408," Investigate Radiology, 1998, 33(12), 880-885.
Xie, et al., "Acute Myocardial Ischemia and Reperfusion can be Visually Identified Non-invasively with Intravenous Perfluoropropane-Enhanced Sonicated Dextrose Albumin Ultrasound Contrast", Circulation, vol. 90, No. 4, Part 2, Abstract 2989, Oct. 1994.
Yang et al., "Exposure to Low-Intensity Ultrasound Increases Aggrecan Gene Expression in a Rat Femur Fracture Model." Journal of Orthopaedic Research, vol. 14, No. 5, pp. 802-809, 1996.
Yuda et al., Prolongation of liposome circulation time by various derivatives of polyethyleneglycols. Biol Pharm Bull. Oct. 1996;19(10):1347-51.
Yeung et al., "Preparation of Microencapsulated Liposomes", J. Microencapsulation, 1988, vol. 5, 331-337.
Young et al., "Effect of therapeutic ultrasound on the healing of full-thickness excised skin lesions." Ultrasonics, vol. 28, No. 3, pp. 175-180, 1990.
Young et al., "The Effect of Therapeutic Ultrasound on Angiogenesis." Ultrasound in Medicine and Biology, vol. 16, No. 3, pp. 261-269, 1990.
Yu et al., Incremental value of parametric quantitative assessment of myocardial perfusion by triggered Low-Power myocardial contrast echocardiography. J Am Coll Cardiol. May 19, 2004;43(10):1807-13.
Yu, S.-H., et al., "Effect of pulmonary surfactant protein B (SP-B) and calcium on phospholipids adsorption and squeeze-out of phosphatidylglycerol frombinary phospholipids monolayers containing dipalmitoylphosphatidylcholine," Biochimica et Biophysica Acta, 1992, 1126, 26-34.
Zarif et al., "Synergistic Stabilization of Perfluorocarbon-Pluronic F-68 Emulsion by Perfluoroalkylated Polyhydroxylated Surfactants." JAOCS, vol. 66, No. 10, pp. 1515-1523, 1989.
Zarif, L. et al., "Biodistribution and excretion of a mixed luorocarbon-hydrocarbon "dowel" emulsion as determined by 19-F NMR", Artificial Cells, Blood Substitutes, and Immobilization Biotechnology, 1994, vol. 22,(4) pp. 1193-1198.
Zhou et al., "Targeted delivery of DNA by liposomes and polymers", J. of Controlled Release, vol. 19, pp. 269-274 (1992).
Dams et al., Accelerated blood clearance and altered biodistribution of repeated injections of sterically stabilized liposomes. J Pharmacol Exp Ther. Mar. 2000;292(3):1071-9.
Ishida et al., Accelerated clearance of PEGylated liposomes in rats after repeated injections. J Control Release. Feb. 14, 2003;88(1):35-42.
Millennium Research Group, US contrast agent and radiopharmaceutical market saw a 15 percent decline between 2010 and 2012. Business Wire. Dec. 20, 2012; 3 pages. http://www.businesswire.com/news/home/20121220005837/en/Contrast-Agent-Radiopharmaceutical-Market-15-Percent-Decline [last accessed Aug. 19, 2013].
Frielinghaus et al., End effects in poly(styrene)/poly(ethylene oxide) copolymers. Macromolecules. 2001;34(4):1096-104.
Medved et al., Study of phase equilibriums of aqueous mixtures of polyethylene oxides with terminal groups of different hydrophilicity. Zhumal Prikladnoi Khimii. 1980;53(7)1 669-71. CAPLUS Abstract Accession No. 1980:551033.
Richter et al., Antibodies against polyethylene glycol produced in animals by immunization with monomethoxy polyethylene glycol modified proteins. Int Arch Allergy Appl Immunol. 1983;70(2):124-31.
Richter et al., Polyethylene glycol reactive antibodies in man: titer distribution in allergic patients treated with monomethoxy polyethylene glycol modified allergens or placebo, and in healthy blood donors. Int Arch Allergy Appl Immunol. 1984;74(1):36-9. Abstract Only.
Sherman et al., Role of the methoxy group in immune responses to mPEG-protein conjugates. Bioconjug Chem. Mar. 21, 2012;23(3):485-99. doi: 10.1021/bc200551b. Epub Mar. 7, 2012.
Unsworth et al., Protein-resistant poly(ethylene oxide)-grafted surfaces: chain density-dependent multiple mechanisms of action. Langmuir. Mar. 4, 2008;24(5):1924-9. doi: 10.1021/la702310t. Epub Jan. 25, 2008.
Kitzman et al., Efficacy and safety of the novel ultrasound contrast agent perflutren (Definity) in patients with suboptimal baseline left ventricular echocardiographic images. Am J Cardiol. Sep. 15, 2000;86(6):669-74.
Kurt et al., Impact of contrast echocardiography on evaluation of ventricular function and clinical management in a large prospective cohort. J Am Coll Cardiol. Mar. 3, 2009;53(9):802-10.
Wang et al., Anti-PEG IgM elicited by injection of liposomes is involved in the enhanced blood clearance of a subsequent dose of PEGylated liposomes. J Control Release. Jun. 4, 2007;119(2):236-44. Epub Feb. 24, 2007.

* cited by examiner

PREPARATION OF A LIPID BLEND AND A PHOSPHOLIPID SUSPENSION CONTAINING THE LIPID BLEND

RELATED APPLICATIONS

This application is a continuation of U.S. patent application Ser. No. 13/195,734, filed Aug. 1, 2011, now pending, which is a divisional of U.S. patent application Ser. No. 10/667,931, filed Sep. 22, 2003, now issued as U.S. Pat. No. 8,084,056, which is a continuation of U.S. patent application Ser. No. 09/229,258, filed Jan. 13, 1999, now abandoned, which claims the benefit under 35 U.S.C. §119(e) of U.S. Provisional Patent Application No. 60/071,332, filed Jan. 14, 1998, the entire contents of each of which are incorporated by reference herein.

FIELD OF THE INVENTION

The present invention relates generally to processes for the preparation of a lipid blend and a uniform filterable phospholipid suspension containing the lipid blend, such suspension being useful as an ultrasound contrast agent.

BACKGROUND OF THE INVENTION

Manufacturing of a phospholipid contrast agent can be divided into the following steps: (1) preparation of lipid blend; (2) compounding the bulk solution, which involves the hydration and dispersion of the lipid blend in an essentially aqueous medium to produce a lipid suspension; (3) filtration of the bulk solution through a sterilizing filter(s) to render the suspension free of microbial contaminants; (4) dispensing the sterile suspension into individual vials in a controlled aseptic area; (5) loading the dispensed vials into a lyophilizer chamber to replace the vial headspace gas with perfluoropropane gas (PFP); (6) transferring the sealed vials after gas exchange to an autoclave for terminal sterilization. There are three major obstacles in this process: (1) uniformity of the lipid blend; (2) hydration of the lipid blend; (3) uniformity and particle size of the suspension; and, (4) sterile filtration of the suspension through a sterilizing filter(s).

Phospholipid blends are typically produced by dissolving or suspending the required lipids in an appropriate aqueous or non-aqueous solvent system, and then reducing the volume either by lyophilization or distillation. Ideally, this process produces blended solids with high content uniformity and purity. However, while working well on a small, laboratory scale, this simple approach is frequently problematic upon scale-up to production-size quantities. Difficulties include: (1) maintaining content uniformity during the solvent removal step (due to differential solubilities); (2) maintaining purity (frequently a problem when water is used due to hydrolytic side-reactions); (3) enhancing purity; (4) minimizing solvent volume; and (5) recovery of the final solids (e.g., it is not practical to scrape solids out of a large reactor).

After manufacture of a lipid blend, final compounding typically involves introduction of the blend into an aqueous medium. Since phospholipids are hydrophobic and are not readily soluble in water, adding phospholipids or a lipid blend directly into an aqueous solution causes the lipid powder to aggregate forming clumps that are very difficult to disperse. Thus, the hydration process cannot be controlled within a reasonable process time. Direct hydration of phospholipids or a lipid blend in an aqueous medium produces a cloudy suspension with particles ranging from 0.6 µm to 100 µm. Due to relatively large particle size distribution, the suspension cannot be filtered at ambient temperature when the suspension solution temperature is below the gel-to-liquid crystal phase transition temperatures of lipids. The lipids would accumulate in the filters causing a restriction in the flow rate, and in most cases, the filters would be completely blocked shortly after. Further reduction in the suspension particle size cannot be achieved through a conventional batching process, even after extended mixing (e.g., 6 hours) at elevated temperatures (e.g., 40° C. to 80° C.) with a commonly used marine propeller.

Although filtration at elevated temperatures, i.e., at above the phase transition temperatures of lipids, is possible, a significant amount of larger lipid particles would still be excluded when a normal filtering pressure is used. In turn, concentrations of the sterile filtrate would have variable lipid content from batch to batch depending on how the lipids are initially hydrated which is in turn determined by the physical characteristics, e.g., morphology, of the starting materials.

The process of directly hydrating the lipids or lipid blend to produce a uniform suspension and filtration of the suspension through a sterilization filter(s) can be difficult and costly to be scaled-up to any reasonable commercial scale, e.g., >20 L.

Thus, the presently claimed processes for manufacture of a lipid blend and the subsequent phospholipid suspension are aimed at solving the above issues by providing a practical process that can be easily scaled and adopted to various manufacturing facilities without extensive modification or customization of existing equipment.

SUMMARY OF THE INVENTION

Accordingly, one object of the present invention is to provide a novel process for preparing a lipid blend.

Another object of the present invention is to provide a novel process for preparing a phospholipid suspension from the lipid blend.

These and other objects, which will become apparent during the following detailed description, have been achieved by the inventors' discovery that dissolving a lipid blend in a suitable non-aqueous solvent prior to introduction of an aqueous solution allows for production of a phospholipid suspension.

DETAILED DESCRIPTION OF THE INVENTION

[1] Thus, in a first embodiment, the present invention provides a novel process for preparing a phospholipid suspension, comprising:
  (1) contacting a lipid blend with a non-aqueous solvent, whereby the lipid blend substantially dissolves in the non-aqueous solvent; and,
  (2) contacting the solution from step (1) with an aqueous solution to form a lipid suspension.

[2] In a preferred embodiment, the non-aqueous solvent is selected from propylene glycol, ethylene glycol, and polyethylene glycol 300.

[3] In a more preferred embodiment, the non-aqueous solvent is propylene glycol.

[4] In another preferred embodiment, the lipid blend, comprises:
  (a) 1,2-dipalmitoyl-sn-glycero-3-phosphatidylcholine;
  (b) 1,2-dipalmitoyl-sn-glycero-3-phosphotidic, mono sodium salt; and,
  (c) N-(methoxypolyethylene glycol 5000 carbamoyl)-1,2-dipalmitoyl-sn-glycero-3-phosphatidylethanolamine, mono sodium salt.

[5] In another preferred embodiment, in step (1), the non-aqueous solvent is heated to a temperature of about 30 to 70° C. prior to contacting with the lipid blend.

[6] In another more preferred embodiment, the non-aqueous solvent is heated to a temperature of about 50 to 55° C. prior to contacting with the lipid blend.

[7] In another preferred embodiment, the ratio of lipid blend to non-aqueous solvent is from about 5 mg of lipid blend per mL of non-aqueous solvent to about 15 mg/mL.

[8] In another more preferred embodiment, the ratio of lipid blend to non-aqueous solvent is about 10 mg/mL.

[9] In another preferred embodiment, in step (2), the aqueous solution is selected from water, saline, a saline/glycerin mixture, and a saline/glycerin/non-aqueous solvent mixture.

[10] In another more preferred embodiment, the aqueous solution is a saline and glycerin mixture.

[11] In another more preferred embodiment, the aqueous solution is a saline, glycerin, and propylene glycol mixture.

[12] In another more preferred embodiment, 6.8 mg/mL of sodium chloride are present, 0.1 mL/mL of glycerin are present, 0.1 mL/mL of propylene glycol are present, and about 0.75 to 1.0 mg/mL of the lipid blend are present.

[13] In an even more preferred embodiment, 0.75 mg/mL of lipid blend are present.

[14] In another more preferred embodiment, 1.0 mg/mL of lipid blend are present.

[15] In another preferred embodiment, in step (2), the aqueous solution is heated to a temperature of about 45 to 60° C. prior to contacting with the solution from step (1).

[16] In another more preferred embodiment, the aqueous solution is heated to a temperature of about 50 to 55° C. prior to contacting with the solution from step (1).

[17] In another preferred embodiment, the process further comprises:
  (3) heating the lipid suspension from step (2) to a temperature about equal to or above the highest gel to liquid crystalline phase transition temperature of the lipids present in the suspension.

[18] In another more preferred embodiment, in step (3), the lipid suspension is heated to a temperature of at least about 67° C.

[19] In another more preferred embodiment, the process further comprises:
  (4) filtering the lipid suspension through a sterilizing filter.

[20] In another even more preferred embodiment, in step (4), the filtration is performed using two sterilizing filter cartridges.

[21] In a further preferred embodiment, in step (4), the sterilizing filter cartridges are at a temperature of from about 70 to 80° C.

[22] In another further preferred embodiment, in step (4), 0.2 μm hydrophilic filters are used.

[23] In another even more preferred embodiment, the process further comprises:
  (5) dispensing the filtered solution from step (4) into a vial.

[24] In another further preferred embodiment, the process further comprises:
  (6) exchanging the headspace gas of the vial from step (5) with a perfluorocarbon gas.

[25] In another even further preferred embodiment, the perfluorocarbon gas is perfluoropropane.

[26] In another even further preferred embodiment, exchange of headspace gas is performed using a lyophilizing chamber.

[27] In another even further preferred embodiment, the process further comprises:
  (7) sterilizing the vial from step (6).

[28] In a still further preferred embodiment, in step (7), the vial is sterilized at about 126-130° C. for 1 to 10 minutes.

[29] In a second embodiment, the present invention provides a novel process for preparing a lipid blend, comprising:
  (a) contacting at least two lipids with a first non-aqueous solvent;
  (b) concentrating the solution to a thick gel;
  (c) contacting the thick gel with a second non-aqueous solvent; and,
  (d) collecting the resulting solids.

[30] In a preferred embodiment, in step (a), the lipids are:
  (i) 1,2-dipalmitoyl-sn-glycero-3-phosphatidylcholine;
  (ii) 1,2-dipalmitoyl-sn-glycero-3-phosphotidic, mono sodium salt; and,
  (iii) N-(methoxypolyethylene glycol 5000 carbamoyl)-1,2-dipalmitoyl-sn-glycero-3-phosphatidylethanolamine, mono sodium salt.

[31] In another preferred embodiment, in step (a), the first non-aqueous solvent is a mixture of methanol and toluene.

[32] In another preferred embodiment, in step (c), the second non-aqueous solvent is a methyl t-butyl ether.

[33] In another preferred embodiment, in step (a), the solution is warmed to a temperature sufficient to complete dissolution of the lipids into the solvent.

[34] In another more preferred embodiment, in step (a), the solution is warmed to about 25 to 75° C.

[35] In another preferred embodiment, in step (d), the solids collected are washed with methyl t-butyl ether and dried in vacuo.

[36] In a third embodiment, the present invention provides a novel phospholipid suspension, comprising:
  (a) a lipid blend in an amount of about 0.75-1.0 mg/mL of suspension;
  (b) sodium chloride in an amount of about 6.8 mg/mL of suspension;
  (c) glycerin in an amount of about 0.1 mL/mL of suspension;
  (d) propylene glycol in an amount of about 0.1 mL/mL of suspension; and
  (e) water;
wherein the suspension is prepared by the process, comprising:
  (1) contacting a lipid blend with a non-aqueous solvent, whereby the lipid blend substantially dissolves in the non-aqueous solvent;
  (2) contacting the solution from step (1) with an aqueous solution to form a lipid suspension;
  (3) heating the lipid suspension from step (2) to a temperature about equal to or above the highest gel to liquid crystalline phase transition temperature of the lipids present in the suspension; and,
  (4) filtering the lipid suspension through a sterilizing filter.

[37] In another preferred embodiment, the lipid blend, comprises:
  (a) 1,2-dipalmitoyl-sn-glycero-3-phosphatidylcholine;

(b) 1,2-dipalmitoyl-sn-glycero-3-phosphotidic, mono sodium salt; and, (c) N-(methoxypolyethylene glycol 5000 carbamoyl)-1,2-dipalmitoyl-sn-glycero-3-phosphatidylethanolamine, mono sodium salt.

[38] In another more preferred embodiment, the non-aqueous solvent is heated to a temperature of about 50 to 55° C. prior to contacting with the lipid blend.

[39] In another more preferred embodiment, the ratio of lipid blend to non-aqueous solvent is about 10 mg/mL.

[40] In another more preferred embodiment, the aqueous solution is a saline, glycerin, and propylene glycol mixture.

[41] In an ever more preferred embodiment, 0.75 mg/mL of lipid blend are present.

[42] In another more preferred embodiment, the aqueous solution is heated to a temperature of about 50 to 55° C. prior to contacting. with the solution from step (1).

[43] In another more preferred embodiment, in step (3), the lipid suspension is heated to a temperature of at least about 67° C.

[44] In another further preferred embodiment, in step (4), two 0.2 μm hydrophilic filters are used.

Formulation

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Lipid blend or phospholipid blend, as used herein, is intended to represent two or more lipids which have been blended. The lipid blend is generally in a powder form. Preferably, at least one of the lipids is a phospholipid. Preferably, the lipid blend contains 1,2-dipalmitoyl-sn-glycero-3-phosphatidylcholine (DPPC), 1,2-dipalmitoyl-sn-glycero-3-phosphotidic, mono sodium salt (DPPA), and N-(methoxypolyethylene glycol 5000 carbamoyl)-1,2-dipalmitoyl-sn-glycero-3-phosphatidylethanolamine, monosodium salt (MPEG5000-DPPE). The amount of each lipid present in the blend will depend on the desired end product. Preferred ratios of each lipid are described in the Examples section. A wide variety of other lipids, like those described in Unger et al, U.S. Pat. No. 5,469,854, the contents of which are hereby incorporated by reference, may be used in the present process.

Phospholipid, as used herein, is a fatty substance containing an oily (hydrophobic) hydrocarbon chain(s) with a polar (hydrophilic) phosphoric head group. Phospholipids are amphiphilic. They spontaneously form boundaries and closed vesicles in aqueous media. Phospholipids constitute about 50% of the mass of animal cell plasma membrane.

Preparation of the Lipid Blend

The lipid blend may be prepared via an aqueous suspension-lyophilization process or an organic solvent dissolution-precipitation process using organic solvents. In the aqueous suspension-lyophilization process, the desired lipids are suspended in water at an elevated temperature and then concentrated by lyophilization. Preferably a dissolution procedure is used.

Step (a):

The organic solvent dissolution-precipitation procedure involves contacting the desired lipids (e.g., DPPA, DPPC, and MPEG5000 DPPE) with a first non-aqueous solvent system. This system is typically a combination of solvents, for example $CHCl_3$/MeOH, $CH_2Cl_2$/MeOH, and toluene/MeOH. Preferably, the first non-aqueous solvent is a mixture of toluene and methanol. It may be desirable to warm the lipid solution to a temperature sufficient to achieve complete dissolution. Such a temperature is preferably about 25 to 75° C., more preferably about 35 to 65° C.

After dissolution, it may be desired to remove undissolved foreign matter by hot-filtration or cooling to room temperature and then filtering. Known methods of filtration may be used (e.g., gravity filtration, vacuum filtration, or pressure filtration).

Step (b):

The solution is then concentrated to a thick gel/semisolid. Concentration is preferably done by vacuum distillation. Other methods of concentrating the solution, such as rotary evaporation, may also be used. The temperature of this step is preferably about 20 to 60° C., more preferably 30 to 50° C.

Step (c):

The thick gel/semisolid is then dispersed in a second non-aqueous solvent. The mixture is slurried, preferably near ambient temperature (e.g., 15-30° C.). Useful second non-aqueous solvents are those that cause the lipids to precipitate from the filtered solution. The second non-aqueous solvent is preferably methyl t-butyl ether (MTBE). Other ethers and alcohols may be used.

Step (d):

The solids produced upon addition of the second non-aqueous solvent are then collected. Preferably the collected solids are washed with another portion of the second non-aqueous solvent (e.g., MTBE). Collection may be performed via vacuum filtration or centrifugation, preferably at ambient temperature. After collection, it is preferred that the solids are dried in vacuo at a temperature of about 20-60° C.

For the following reasons, the organic solvent dissolution-precipitation process is preferred over the aqueous suspension/lyophilization process:

(1) Because the lipids are quite soluble in toluene/methanol, solvent volumes are significantly reduced (relative to the aqueous procedure).

(2) Because of this increased solubility, the process temperature is also lower relative to the aqueous procedure, thereby avoiding the hydrolytic instability of fatty acid esters.

(3) When cooled back to room temperature, the toluene/methanol solution of lipids remains homogeneous, allowing a room temperature filtration to remove solid foreign matter.

(4) The MTBE precipitation allows quick and easy isolation of Lipid Blend solids. With the aqueous process, a time-consuming lyophilization process is used to isolate material.

(5) The MTBE precipitation also allows for the removal of any MTBE-soluble impurities, which go into the filtrate waste-stream. This potential for impurity removal is not realized when a solution is directly concentrated or lyophilized to a solid.

(6) The present process affords uniform solids.

Preparation of the Lipid Suspension

Step (1):

In step one, a lipid blend is contacted with a non-aqueous solvent, whereby the lipid blend substantially dissolves in the non-aqueous solvent. Alternatively, the individual lipids may be contacted with the non-aqueous solvent sequentially in the order: DPPC, DPPA, and MPEG5000-DPPE; DPPC, MPEG5000-DPPE, and DPPA; MPEG5000-DPPE, DPPA, and DPPC; or MPEG5000-DPPE, DPPC, and DPPA. The DPPA, being the least soluble and least abundant of the lipids is not added first. Adding one of the other lipids prior to or concurrently with adding the DPPA facilitates dissolution of the DPPA. In another alternative, the individual lipids can be combined in their solid forms and the combination of the solids contacted with the non-aqueous solvent.

Substantial dissolution is generally indicated when the mixture of lipid blend and non-aqueous solvent becomes clear. As noted previously, phospholipids are generally not water soluble. Thus, direct introduction of a blend of phospholipid blend into an aqueous environment causes the lipid blend to aggregate forming clumps that are very difficult to disperse. The present invention overcomes this limitation by dissolving the lipid blend in a non-aqueous solvent prior to introduction of the aqueous solution. This allows one to evenly disperse the lipid blend into a liquid. The liquid dispersion can then be introduced into a desired aqueous environment.

Non-aqueous is intended to mean a solvent or mixture of solvents wherein the amount of water present is sufficiently low as to not impede dissolution of the lipid blend. The amount of non-aqueous solvent required will depend on the solubility of the lipid blend and also the final desired concentration of each component. As one of ordinary skill would appreciate, the level of water present in the non-aqueous solvent, which may be tolerated will vary based on the water solubilities of the individual lipids in the lipid blend. The more water soluble the individual phospholipids, the more water which may be present in step (1). Preferably, propylene glycol is used as the non-aqueous solvent. However, other members of the polyol family, such as ethylene glycol, and polyethylene glycol 300 may be used.

Mechanically mixing the lipid blend and non-aqueous solvent may be necessary to achieve complete dissolution. One of ordinary skill in the art will recognize that a variety of ways of mixing are available. It is preferred that a high shear homogenizer is used.

One of ordinary skill in the art would recognize that raising the temperature of the solvent should aid in dissolution of the lipid blend. The temperature at which step (1) may be performed can range from ambient to the boiling point of the chosen solvent. Preferably the temperature is from about 30 to about 70° C., more preferably about 45 to about 60° C., and even more preferably about 50, 51, 52, 53, 54, or 55° C. When ethylene glycol or polyethylene glycol 300 is used, it is preferred that the temperature be from about 50 to about 60° C. and more preferably about 55° C. Maintaining the solution at an elevated temperature should reduce solution viscosity and ease formulation preparation.

A preferred procedure for dissolving the lipid blend is as follows: (a) Add propylene glycol to an appropriate weighing container. (b) Warm the propylene glycol to about 40-80° C. in a heating bath. (c) Weigh the lipid blend into a separate container. (d) When the propylene glycol has reached the desired temperature range, transfer the solution into the container containing the lipid blend. (e) Place the container back into the heating bath until the solution is clear. (f) Mechanically mix the Lipid Blend/Propylene Glycol solution to further assure complete dissolution and uniform dispersion of the lipid blend.

The ratio of lipid blend to non-aqueous solvent will, of course, be limited by the solubility of the lipid blend. This ratio will also be influenced by the desired amount of lipid blend in the final formulation. Preferably, the ratio is from about 1 mg of lipid blend per mL of solvent (mg/mL) to about 100 mg/mL. More preferably, the lipid blend is present in about 5, 6, 7, 8, 9, 10, 11, 12, 13, 14, or 15 mg/mL. Even more preferably, the lipid blend is present in about 10 mg/mL.

Step (2):

The second step involves contacting the solution from step (1) with an aqueous solution to form a lipid suspension. The aqueous solution can be water, saline, a saline/glycerin mixture or a saline/glycerin/non-aqueous solvent mixture. Non-aqueous solvent is as defined previously, preferably propylene glycol. Suspension, as used herein, is intended to indicate a dispersion in which insoluble particles are dispersed in a liquid medium.

Once complete dissolution of the lipid blend has been achieved (step (1)), the resulting solution can then be introduced to an aqueous solution. The aqueous solution may contain one or more components selected from sodium chloride, glycerin, and a non-aqueous solvent. Preferably the aqueous solution contains glycerin and sodium chloride. Preferably, a sufficient amount of propylene glycol is present in the aqueous solution, prior to addition of the solution from step 1, in order to achieve the final desired concentration of propylene glycol.

The order of addition of desired components is not expected to seriously impact the resulting lipid suspension. However, it is preferred that the lipid-blend solution is added to water, which may already contain the above-noted additional components. Additional desired components can then be added. It is more preferred that the lipid-blend solution is added a solution of water and sodium chloride (i.e., saline). It is further preferred that the lipid-blend solution is added a solution of water, sodium chloride, and glycerin. It is still further preferred that the lipid-blend solution is added a solution of water, sodium chloride, glycerin, and propylene glycol.

It is preferred that 6.8 mg of NaCl are present per mL of formulation. Preferably, 0.1 mL of Glycerin per mL of formulation is present. A final concentration of 0.1 mL of Propylene Glycol per mL of formulation is preferred. The final pH of the formulation is preferably about 5.5-7.0.

The lipid blend is preferably present in an amount of 0.75-1.0 mg/mL of formulation.

The temperature of the aqueous solution can range from ambient to 70° C. Preferably, the temperature is about 45 to 60° C., with 50, 51, 52, 53, 54, or 55 being even more preferred. In order to obtain complete dissolution, the mixture will need to be agitated, preferably stirred. Also, the pH of the solution may need to be adjusted, depending on the desired final formulation. Either acid (e.g., HCl) or base (e.g., NaOH) can be added to make such an adjustment.

The lipid suspension will contain liquid particles of varying sizes. One of the benefits of the present invention is the ability to consistently obtain small particles of a nearly uniform size. Thus, it is preferred that the majority of particles obtained are less than 100 nm in diameter, more preferable less than 50 nm.

A preferred procedure for dissolving the lipid blend is as follows: (a) Add Water for Injection (WFI) into a compounding vessel. (b) Start mixing and ensure temperature is from 50-55° C. (c) Add sodium chloride to the compounding vessel. Wait until the solid has completely dissolved before proceeding to the next step. (d) Add glycerin to the compounding vessel. Allow sufficient time for complete mixing. (e) Add the remaining Propylene Glycol that is not in the Lipid Blend/Propylene Glycol solution. Allow time for thorough mixing. (f) Reduce mixing rate to reduce turbulence in the compounding vessel. (g) Add the Lipid Blend/Propylene Glycol solution to the compounding vessel. (h) Readjust mixing to original rate. (i) Add additional WFI if necessary. (j) Continue to mix for approximately 25 minutes and assure complete mixing. (k) Verify and adjust the solution to target pH.

Step(3):

Step three involves heating the lipid suspension obtained from step (2) to a temperature about equal to or above the highest gel to liquid crystalline phase transition temperature of the lipids present in the solution.

One of the objects of this step is to provide a filterable suspension. A solution/suspension is considered filterable if there is no significant reduction in flow rate within a normal process, and there is no significant increase in the pressure drop in the filtration system.

Experimental data indicates that the lipids in the formulation should be beyond their gel to liquid crystalline phase transition in order to simplify sterile filtration. When the lipids are below the phase transition temperature, the suspension particles are rigid. However, when they are above their respective gel-liquid crystal phase transition temperatures, they are in a more loosely organized configuration and thus, more easily filtered.

DPPC and DPPA show phase transitions of 41° C. and 67° C. respectively. MPEG5000-DPPE is soluble in water, therefore it does not exhibit a gel-liquid crystal phase transition which is characteristic of most hydrated lipid suspensions. Because the lipids in the preferred formulation all exhibit different gel to liquid phase transitions, the highest phase transition temperature, 67° C., is preferably used to filter the solution. By maintaining temperature at or beyond 67° C., all the lipids are beyond their respective phase transition, assuring the loose configuration while passing through the filters.

Heating may be achieved by jacketing the compounding vessel with a heat exchanging coil. Hot water/steam from a controlled source, e.g., a hot water bath, or a water heater, would deliver sufficient heat to maintain the compounding solution at a set temperature. Other heat sources known to those of skill in the art could also be used.

Step (4):

Step four is performed by filtering the lipid suspension through a sterilizing filter. The purpose behind this step being to provide a substantially bacteria-free suspension. A filtrate is considered substantially bacteria-free when the probability of the filtrate to contain at least one colony forming microorganism is less than $10^{-6}$.

Filtration is preferably done using sterilizing filter cartridges. Also, a means of forcing the solution through the filters may be required (e.g., pumping or pressurizing). Since the solution being filtered needs to be maintained at a temperature at or above the highest gel to liquid crystalline phase transition temperature of the lipids present in the solution, the filtration should be performed at about this same temperature. In order to accomplish this, the filter (e.g., sterilizing filter cartridges) are preferably enclosed in jacketed filter housings which are continuously heated, e.g., by a hot water stream from a temperature controlled water bath, to ensure that the suspension is above the lipid phase transition temperatures. The temperature of the sterilizing filter is preferably from 50 to 100° C., more preferably from 60 to 90° C., and even more preferably 70, 71, 72, 73, 74, 75, 76, 77, 78, 79, or 80° C.

One or more sterilizing filters may be used to filter the suspension. The required number will be based on their effectiveness at removing bacteria. It is preferred that two filters are used. The size of the filter pores will be limited by the need to provide a bacteria-free suspension. Preferably, 0.2 μm hydrophilic filters are used.

A bulk solution of the preferred formulation was continuously filtered through two 0.2 μm hydrophilic filters for up to 3 hours at a rate of approximately 1 liter per minute (1 L/min.), i.e., passing a total of 180 liters of the suspension solution through the filters. The experimental results shows that there is no apparent blockage of filters. Lipid assays indicates that there is no measurable loss during the filtration process (due to accumulation in the filter medium).

A bulk solution of the preferred formulation was compounded at 40° C.-80° C., and the suspension was cooled to ambient temperature prior to sterile filtration. No apparent clogging of the filters were observed indicating the suspension particle size distribution is well below 0.2 μm of the filter pore size. It is desirable to use heat during filtration in order to ensure maximum recover of the lipid blend in the sterile filtrate (i.e., to minimize potential retention of lipid particles in the filter medium).

A preferred procedure for filtering the lipid suspension is as follows: (a) Assure all jacketed filters are at 70° C.-80° C. (b) Assure all valves in the filtration unit are closed. (c) Connect filtration inlet hose to the outlet of the compounding vessel. (d) Open valves to allow solution to pass through the filters. (e) Flush three liters of solution through the filters before collecting filtrate. (f) Continue filtration until complete.

Step (5):

Dispensing the filtered solution into a vial completes step five. Preferably, this step is performed in a controlled aseptic area. One of ordinary skill in the art would recognize that the vial selected and amount of suspension delivered to the vial would depend on the end use considered for the lipid suspension. Dispensing can be achieved via a variety of methods, including pipette, hand-held syringe dispenser (e.g., Filamatic® syringe dispensing machine), or industrial auto dispensing machine (e.g., Cozzoli or TL auto filling machine).

Step (6):

Step six is performed by exchanging the headspace gas of the vials from step five with a perfluorocarbon gas. A preferred method of exchange is to load the dispensed vials into a lyophilizer chamber and replace the vial headspace gas with a perfluorocarbon gas. A preferred gas is perfluoropropane (PFP). Other methods of headspace gas exchange known to those of skill in the art may be employed.

The vials are sealed at the completion of the vial headspace gas exchange cycle. When the lyophilizer chamber pressure is brought back to atmospheric pressure by charging into the chamber with PFP. Vial stoppers are seated to seal the vials.

Step (7):

Step seven involves terminally sterilizing a vial after step six. One method of terminal sterilization is through the use of an autoclave. Also, the sealed vials can be terminally sterilized in a steam sterilizer to further enhance the sterility assurance of the product. Care must be taken in the sterilization process as some degradation of lipids may be observed as a result of autoclaving. Preferably, the vial is sterilized at about 126-130° C. for 1 to 10 minutes.

Other features of the invention will become apparent in the course of the following descriptions of exemplary embodiments which are given for illustration of the invention and are not intended to be limiting thereof.

EXAMPLES

TABLE 1

| Lipid Blend Target Composition | | | |
|---|---|---|---|
| Lipid Name | Common Name | Wt % | Mole % |
| DPPA | 1,2-dipalmitoyl-sn-glycero-3-phosphatidic acid, monosodium salt | 6.0 | 10 |
| DPPC | 1,2-dipalmitoyl-sn-glycero-3-phosphatidylcholine | 53.5 | 82 |
| MPEG5000 DPPE | N-(methoxypolyethylene glycol 5000 carbamoyl)-1,2-dipalmitoyl-sn-glycero-3-phosphatidylethanolamine, monosodium salt | 40.5 | 8 |

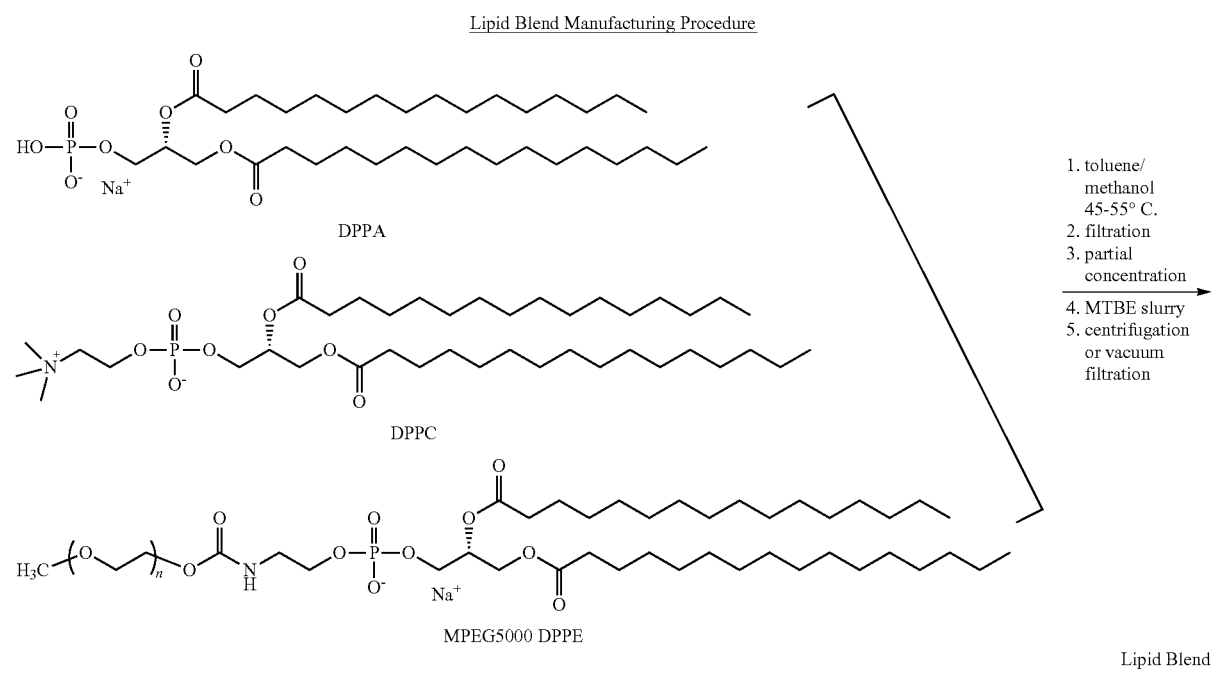

Lipid Blend Manufacturing Procedure

A flask is charged with toluene (3.3 L), methanol (1.2 L), DPPA (59.6 g), DPPC (535 g), and MPEG5000 DPPE (405 g). After rinsing solid contact surfaces with 0.9 L methanol, the slurry is warmed to 45-55° C. until dissolution is complete.

The solution is filtered and then concentrated in vacuo at 35-45° C. to a thick gel. Methyl t-butyl ether (MTBE, 5.4 L) is added and the mixture is slurried at 15-30° C. White solids are collected by centrifugation or vacuum filtration, and washed with MTBE (0.9 L). The solids are then placed in a vacuum oven and dried to constant weight at 40-50° C. The dried Lipid Blend is transferred to a bottle and stored at -15 to -25° C.

In another embodiment of the lipid blend manufacturing procedure of the present invention, the following procedure may also be used.

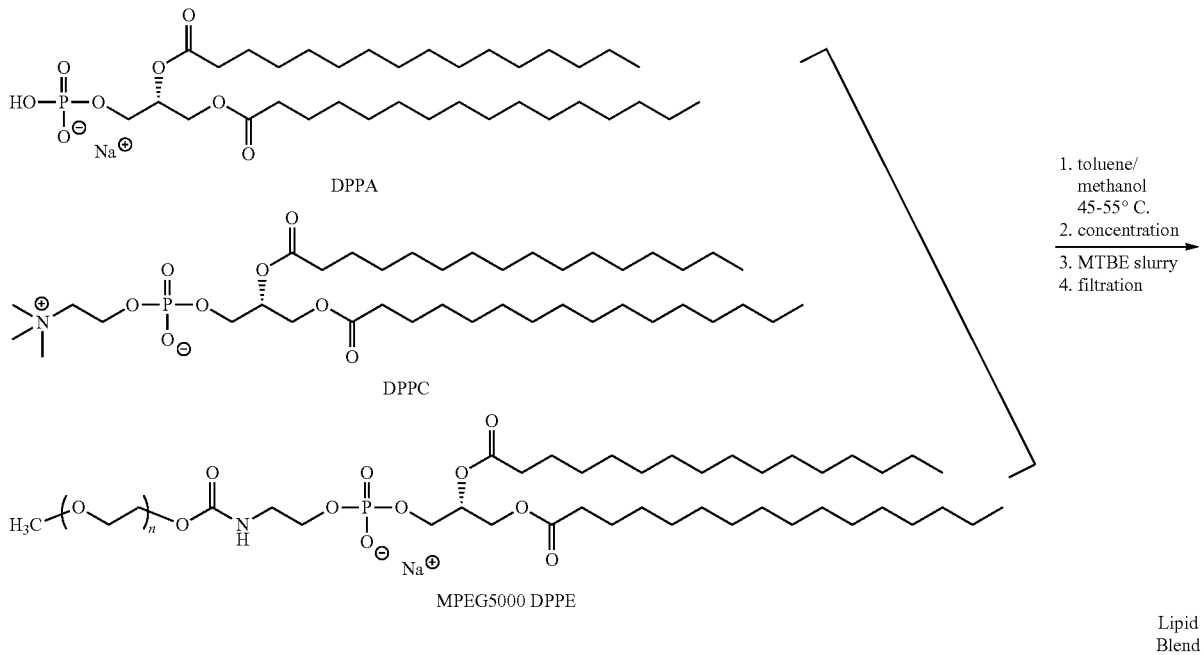

Phospholipid quantities were adjusted for purity based on a "Use As" value from the certificates of analysis. The batch size (combined phospholipid weight) of this experiment was 2 kg.

A rotary evaporation flask is charged sequentially with toluene (3,300 mL), methanol (1,200 mL), DPPA (122.9 g; corrected for "use as" purity of 97.0%), DPPC (1,098.5 g total; 500.8 g from a lot with 98.4% "use as" purity and 597.7 g from a lot with 96.7% "use as" purity), and MPEG5000 DPPE (815.7 g; corrected for "use as" purity of 99.3%). After rinsing residual solids into the flask with methanol (900 mL), the flask is placed on a rotary evaporator (no vacuum) and the slurry is warmed to between 45 and 55° C. (external). After dissolution is complete, the external temperature is reduced to between 35 and 45° C., a vacuum is applied, and the solution is concentrated to a white semi-solid. The flask is removed from the evaporator and solids are broken up with a spatula. The flask is reapplied to the evaporator and concentration is continued. After reaching the endpoint (final vacuum pressure$^2$ 20 mbar; white, granular, chunky solid), MTBE (5,400 mL) is added through the rotary evaporator's addition tube, the vacuum is discontinued, and the mixture is slurried for 15 to 45 min at 15 to 30° C. Solids are isolated by either centrifugal or vacuum filtration, rinsed with MTBE (3,800 mL), and dried to constant weight in a vacuum oven (40 to 50° C.). Prior to transferring to polyethylene bottles with polypropylene caps, solids are delumped through a screen (0.079 inch mesh), affording 1,966.7 g (98%) of lipid blend (SG896) as a white solid.

The preferred lipid suspension contains:
1,2-dipalmitoyl-sn-glycero-3-phosphotidic, mono sodium salt (DPPA);
1,2-dipalmitoyl-sn-glycero-3-phosphatidylcholine (DPPC);
N-(methoxypolyethylene glycol 5000 carbamoyl)-1,2-dipalmitoyl-sn-glycero-3-phosphatidylethanolamine, monosodium salt (MPEG5000-DPPE);
Propylene Glycol, USP;
Glycerin, USP;
Sodium Chloride, USP; and,
Water for Injection, USP.

TABLE 2

Preferred Contrast Agent Formulations

| Component | A* | B* |
|---|---|---|
| NaCl, USP | 6.8 mg/mL | 6.8 mg/mL |
| Glycerin, USP | 0.1 mL/mL | 0.1 mL/mL |
| Propylene Glycol, USP | 0.1 mL/mL | 0.1 mL/mL |
| Lipid Blend** | 1 mg/mL | 0.75 mg/mL |
| Perfluoropropane | >65% | >65% |
| pH | 6.0-7.0 | 6.0-7.0 |

*Formulation A has 1 mg/mL lipid blend. Formulation B has a lipid blend concentration of 0.75 mg/mL.
**The lipid blend is consist of 53.5 wt. % of DPPC, 6.0 wt. % of DPPA and 40.5 wt. % of MPEG5000-DPPE.

TABLE 3

Preferred Container and Closure

| Component | Type |
|---|---|
| Vial | Wheaton 2802, B33BA, 2 cc, 13 mm, Type I, flint tubing vial |

TABLE 3-continued

Preferred Container and Closure

| Component | Type |
|---|---|
| Stopper | West V50 4416/50, 13 mm, gray butyl lyo, siliconized stoppers |
| Seal | West 3766, white 13 mm, flip-off aluminum seals |

The finished product fill volume can be from 1.0-2.0 mL/vial.

In the preparation of the preferred formulation, when the lipid blend is directly hydrated with the aqueous matrix solution containing water for injection, sodium chloride, glycerin and propylene glycol, the filtrates have less lipids as compared to the pre-filtration bulk solution. The loss of lipids varies from 12% to 48%. These results demonstrate that the sterile filtration process is not effectively controlled, and therefore, the final product lipid content is highly variable.

In contrast, using the presently described process, assay results of the lipids in show full recovery of lipids during the filtration process. Variability of assay results around the theoretical targets is within normal assay method variability. Particle size distribution by number, by volume and by reflective intensity of a suspension prepared by first solubilizing lipid blend in propylene glycol indicate that the majority of the particles are less than 50 nm in the pre-filtered bulk solution at 55° C. as well at 70° C. The particle distribution profile does not change after filtration.

Utility Section

The presently claimed process is useful for preparing ultrasound contrast agents. Such agents should be useful for a variety of imaging applications, including enhancing contrast in echocardiographic and radiologic ultrasound images.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of the United States is:

1. A method comprising
   (a) formulating a lipid suspension with a perfluorocarbon gas to form an ultrasound contrast agent, and
   (b) using the ultrasound contrast agent in an imaging application in a subject, wherein the lipid suspension is made by
   (i) contacting phospholipids 1,2-dipalmitoyl-sn-glycero-3-phosphatidic acid, mono sodium salt (DPPA), 1,2-dipalmitoyl-sn-glycero-3-phosphatidylcholine (DPPC), and N-(methoxypolyethylene glycol 5000 carbamoyl)-1,2-dipalmitoyl-sn-glycero-3-phosphatidylethanolamine, mono sodium salt (MPEG5000-DPPE) with a first non-aqueous solvent to form a lipid solution, wherein contacting comprises
      (1) sequential addition of the individual phospholipids to the first non-aqueous solvent or
      (2) combining the individual phospholipids with each other prior to their addition to the first non-aqueous solvent;
   (ii) contacting the lipid solution of (i) with a second non-aqueous solvent which causes the phospholipids to precipitate out as a solid lipid blend;
   (iii) collecting the solid lipid blend;
   (iv) contacting the solid lipid blend with a third non-aqueous solvent which causes the lipid blend to dissolve to form a lipid blend solution; and
   (v) contacting the lipid blend solution with an aqueous solution to yield the lipid suspension.

2. The method of claim 1, wherein the first non-aqueous solvent is a mixture of methanol and toluene.

3. The method of claim 1, wherein the second non-aqueous solvent is methyl t-butyl ether.

4. The method of claim 1, wherein the third non-aqueous solvent is propylene glycol.

5. The method of claim 1, wherein the aqueous solution comprises sodium chloride, glycerin, and propylene glycol.

6. The method of claim 1, wherein
   (i) the first non-aqueous solvent is a mixture of methanol and toluene;
   (ii) the second non-aqueous solvent is methyl t-butyl ether;
   (iii) the third non-aqueous solvent is propylene glycol; and
   (iv) the aqueous solution comprises sodium chloride, glycerin and propylene glycol.

7. The method of claim 1, wherein about 0.75 to 1.0 mg of the lipid blend is present per mL of the lipid suspension.

8. The method of claim 1, wherein about 0.75 mg of the lipid blend is present per mL of the lipid suspension.

9. The method of claim 1, wherein the third non-aqueous solvent is heated to a temperature of about 30 to 70° C. prior to contacting with the solid lipid blend.

10. The method of claim 1, wherein the third non-aqueous solvent is heated to a temperature of about 50 to 55° C. prior to contacting with the solid lipid blend.

11. The method of claim 1, wherein the ratio of solid lipid blend to third non-aqueous solvent is from about 5-15 mg of solid lipid blend per mL of third non-aqueous solvent.

12. The method of claim 1, wherein the ratio of solid lipid blend to third non-aqueous solvent is about 15 mg of solid lipid blend per mL of third non-aqueous solvent.

13. The method of claim 1, wherein the aqueous solution is heated to a temperature of about 45 to 60° C. prior to contacting with the lipid blend solution.

14. The method of claim 1, wherein the aqueous solution is heated to a temperature of about 50 to 55° C. prior to contacting with the lipid blend solution.

15. The method of claim 1, further comprising filtering the lipid suspension through one or two sterilizing filters to form a filtered lipid suspension, prior to formulating with the perfluorocarbon gas.

16. The method of claim 15, wherein the one or two sterilizing filters are 0.2 μm filters.

17. The method of claim 15, further comprising dispensing the filtered lipid suspension into a vial, prior to formulating with the perfluorocarbon gas.

18. The method of claim 1, wherein formulating the lipid suspension with the perfluorocarbon gas comprises dispensing the lipid suspension into a vial and exchanging headspace gas of the vial with the perfluorocarbon gas, wherein the lipid suspension is a filtered lipid suspension.

19. The method of claim 1, wherein the perfluorocarbon gas is perfluoropropane.

20. The method of claim 18, wherein the perfluorocarbon gas is perfluoropropane.

21. The method of claim 18, further comprising sterilizing the vial.

22. The method of claim 21, wherein the vial is sterilized at about 126-130° C. for 1 to 10 minutes.

23. The method of claim 1, wherein
(i) the third non-aqueous solvent is heated to a temperature of about 50-55° C. prior to contacting with the solid lipid blend; and
(ii) the aqueous solution is heated to a temperature of about 50-55° C. prior to contacting with the lipid blend solution.

24. The method of claim 6, wherein the lipid suspension comprises about 0.75-1.0 mg of the lipid blend per mL of the lipid suspension.

25. The method of claim 1, wherein the lipid suspension comprises MPEG5000-DPPE, DPPA and DPPC in a mole % ratio of 8 to 10 to 82.

26. The method of claim 7, wherein the lipid suspension comprises MPEG5000-DPPE, DPPA and DPPC in a mole % ratio of 8 to 10 to 82.

27. The method of claim 24, wherein the lipid suspension comprises MPEG5000-DPPE, DPPA and DPPC in a mole % ratio of 8 to 10 to 82.

28. A method comprising:
(a) contacting phospholipids with a first non-aqueous solvent which causes the phospholipids to dissolve and form a lipid solution, wherein the contacting comprises
  (i) sequential addition of the individual phospholipids to the first non-aqueous solvent, or
  (ii) combining the individual phospholipids with each other prior to their addition to the first non-aqueous solvent, and
wherein the phospholipids are 1,2-dipalmitoyl-sn-glycero-3-phosphatidylcholine (DPPC), 1,2-dipalmitoyl-sn-glycero-3-phosphatidic acid, mono sodium salt (DPPA) and N-(methoxypolyethylene glycol 5000 carbamoyl)-1,2-dipalmitoyl-sn-glycero-3-phosphatidylethanolamine, mono sodium salt (MPEG5000-DPPE);
(b) contacting the non-aqueous lipid solution of (a) with a second non-aqueous solvent which causes the phospholipids to precipitate out as a solid lipid blend;
(c) collecting the solid lipid blend;
(d) contacting the solid lipid blend with a third non-aqueous solvent which causes the lipid blend to dissolve to form a lipid blend solution;
(e) contacting the lipid blend solution with an aqueous solution to yield a lipid suspension;
(f) formulating the lipid suspension with a perfluorocarbon gas to form an ultrasound contrast agent; and
(g) using the ultrasound contrast agent in an imaging application in a subject.

* * * * *